US010346590B2

(12) United States Patent
Coughlin et al.

(10) Patent No.: US 10,346,590 B2
(45) Date of Patent: Jul. 9, 2019

(54) PRESCRIPTION STORAGE AND RETRIEVAL SYSTEM

(71) Applicant: ScriptPro LLC, Mission, KS (US)

(72) Inventors: Michael E. Coughlin, Mission, KS (US); Michael E. Skaggs, Mission, KS (US); Ronald A. Leonard, Mission, KS (US); Bradley G. Lockard, Mission, KS (US)

(73) Assignee: SCRIPTPRO LLC, Mission, KS (US)

( * ) Notice: Subject to any disclaimer, the term of this patent is extended or adjusted under 35 U.S.C. 154(b) by 435 days.

(21) Appl. No.: 15/235,278

(22) Filed: Aug. 12, 2016

(65) Prior Publication Data

US 2017/0053099 A1 Feb. 23, 2017

Related U.S. Application Data

(60) Provisional application No. 62/208,297, filed on Aug. 21, 2015, provisional application No. 62/219,220, (Continued)

(51) Int. Cl.
*G07F 11/46* (2006.01)
*G07F 11/42* (2006.01)
*G07F 17/00* (2006.01)
*G06F 19/00* (2018.01)
*G06F 21/31* (2013.01)
*G07F 11/02* (2006.01)
*G16H 20/13* (2018.01)
*G07F 11/62* (2006.01)
(Continued)

(52) U.S. Cl.
CPC ..... *G06F 19/3462* (2013.01); *G05B 19/0426* (2013.01); *G06F 21/31* (2013.01); *G06Q 10/00* (2013.01); *G07F 11/02* (2013.01); *G07F 11/42* (2013.01); *G07F 11/46* (2013.01); *G07F 11/62* (2013.01); *G07F 17/0092* (2013.01); *G16H 20/13* (2018.01); *G05B 2219/25196* (2013.01); *G05B 2219/32287* (2013.01); *G05B 2219/33199* (2013.01)

(58) Field of Classification Search
CPC ................................ G07F 11/46; G07F 11/42
See application file for complete search history.

(56) References Cited

U.S. PATENT DOCUMENTS 5,449,229 A * 9/1995 Aschenbrenner ...... B65G 1/045
221/21
6,155,485 A 12/2000 Coughlin et al.
(Continued)

*Primary Examiner* — Thomas Randazzo
(74) *Attorney, Agent, or Firm* — Hovey Williams LLP

(57) ABSTRACT

A system and method for securely storing and retrieving prescriptions. The system may include storage containers into which the prescriptions may be placed, a storage matrix with an outer housing and compartments for the storage containers, a transport system, scanners, and a control system. The transport system within the outer housing may selectively move the storage containers attached to the attachment device to locations or coordinates of any of the compartments. The control system may command the transport system to relocate any of the storage containers from one of the compartments to another of the compartments and may track locations of the prescriptions based on information from the scanners or other sensors for later retrieval by authorized user.

18 Claims, 29 Drawing Sheets

Related U.S. Application Data filed on Sep. 16, 2015, provisional application No. 62/254,453, filed on Nov. 12, 2015, provisional application No. 62/291,922, filed on Feb. 5, 2016, provisional application No. 62/311,230, filed on Mar. 21, 2016.

(51) Int. Cl.
*G06Q 10/00* (2012.01)
*G05B 19/042* (2006.01)

(56) References Cited

U.S. PATENT DOCUMENTS

| | | | |
|---|---|---|---|
| 6,206,590 B1 | 3/2001 | Thomas et al. | |
| 6,318,630 B1 | 11/2001 | Coughlin et al. | |
| 8,306,651 B2 | 11/2012 | Chudy et al. | |
| 8,342,400 B1* | 1/2013 | Reese | G06F 19/3462 235/385 |
| 8,467,897 B2 | 6/2013 | Holmes et al. | |
| 8,494,672 B2 | 7/2013 | Elmer et al. | |
| 8,583,276 B2 | 11/2013 | Holmes et al. | |
| 8,825,196 B2 | 9/2014 | Holmes et al. | |
| 9,025,275 B1* | 5/2015 | Manes | G11B 15/68 360/92.1 |
| 2004/0105187 A1* | 6/2004 | Woodruff | G11B 15/6825 360/92.1 |
| 2004/0236463 A1* | 11/2004 | Weselak | G11B 15/6835 700/214 |
| 2011/0196538 A1* | 8/2011 | Michael | E05B 47/00 700/275 |
| 2012/0253509 A1* | 10/2012 | Garda | G06F 19/3462 700/235 |
| 2013/0282392 A1* | 10/2013 | Wurm | G06Q 50/22 705/2 |
| 2015/0073585 A1* | 3/2015 | Este | B65G 1/137 700/216 |
| 2016/0257493 A1* | 9/2016 | Astigarraga | B65C 3/26 |

* cited by examiner

PRESCRIPTION STORAGE AND RETRIEVAL SYSTEM

RELATED APPLICATIONS

This patent application claims priority benefit to five provisional patent applications, each incorporated by reference herein in its entirety, including: "Pharmacy Will Call Management System," U.S. Application No. 62/208,297, filed Aug. 21, 2015; "Pharmacy Will Call Management System," U.S. Application No. 62/219,220, filed Sep. 16, 2015; "Pharmacy Will Call Management System," U.S. Application No. 62/254,453, filed Nov. 12, 2015; "Pharmacy Will Call Management System," U.S. Application No. 62/291,922, filed Feb. 5, 2016; and "Pharmacy Will Call Management System," U.S. Application No. 62/311,230, filed Mar. 21, 2016.

BACKGROUND

Pharmacies often fill prescriptions for patients who are not present to immediately receive them. For example, a prescription order may be called or faxed to a pharmacy by doctors so the pharmacy can fill it and have it ready to dispense to the patient or caregiver upon arrival. A pharmacy may also have standing prescription orders on file, requiring ongoing refills of prescriptions as needed over a period of time. Patients may order refills by calling the pharmacy, by accessing the pharmacy's automated interactive voice response (IVR) telephone system, by accessing the pharmacy's website, or by using any number of mobile device applications. Refills may also be triggered automatically by the pharmacy computer system.

Storage systems are often used to store prescriptions until patients arrive. Such systems may be referred to as pharmacy "will call" systems. A common will call system is simply an array of shelves behind the pharmacy counter where prescriptions are placed so pharmacy staff can access them when patients arrive. Busy pharmacies typically have a large number of prescription items in will call. A retail pharmacy that fills 2,000 individual prescriptions per week will typically have approximately 30% of this volume (i.e. 600 prescription items) in will call at any time. Unfortunately, when there are a large number of prescriptions in will call, time is spent searching for the prescriptions needed to dispense to a patient, thus wasting staff time and increasing patient wait time.

Furthermore, many will call storage areas are accessible by anyone behind the pharmacy counter, thus introducing the potential for errors and intentional drug diversion (i.e., theft). For example, prescriptions are sometimes given to the wrong patient due to human error of misreading a label or otherwise selecting the wrong prescription. There is also a greater risk of theft by pharmacy staff or others if the will call storage is not secure.

Thus, there is a need for an improved method of prescription storage and retrieval that mitigates risks of human error, theft, or tampering and decreases retrieval time.

SUMMARY

The present invention solves the above-described problems and provides a distinct advance in the art of will call systems and other prescription storage and retrieval systems. In one embodiment of the invention, a storage and retrieval system includes a storage matrix having an outer housing and a plurality of compartments arranged therein, a plurality of storage containers, a transport system for transporting the storage containers within the storage matrix, scanners for scanning identification indicia on items placed in the storage containers, and a control system.

In some embodiments of the invention, the storage matrix may include at least one access opening formed through its outer housing and selectively accessible by a user. The access openings and the compartments may each be sized and shaped for removably receiving one or more of the storage containers. The storage containers may be sized and shaped to receive and hold items such as standard pharmacy bags or other prescriptions temporarily for patient pickup. The storage containers may fit into the compartments of the storage matrix and be moved between the compartments and/or the access drawers via the transport system. The transport system is located within the outer housing and may detachably attach to the storage containers and selectively move the storage containers to locations or coordinates of any of the compartments or access openings. The scanners may scan identification indicia displayed on items placed in one of the storage containers in the storage matrix. The control system may be communicably coupled with the scanners and the transport system and may command the transport system to relocate any of the storage containers from one of the compartments or access openings to another of the compartments or access openings. The control system may also track locations or coordinates of the items based on the identification indicia on the items, as scanned by the scanners and transmitted to the control system.

In some embodiments of the invention, the control system may receive signals from one of the scanners, corresponding to identification indicia scanned by one of the scanners, indicating that a first item was loaded in a first one of the storage containers in one of the access openings. The control system may further command the transport system to relocate the first one of the storage containers to a selected one of the compartments in the storage matrix that is empty and transmit data that associates identification indicia for the first item and location information for the selected one of the compartments to a memory storage device accessible by the control system. The control system may also receive a request from an authorized user to retrieve the first item, command the transport system to retrieve the first one of the storage containers from the selected one of the compartments, and then command the transport system to move the first one of the storage containers to an empty one of the access openings and deposit the first one of the storage containers into the empty one of the access openings for retrieval of the first item by the authorized user.

In some embodiments of the invention, the storage and retrieval system may additionally include access drawers electronically lockable, actuatable or extendable through the access opening, and movable between an open position and a closed position. The access drawers may be sized and shaped to receive at least one of the storage containers. The control system may also command unlocking of one of the access drawers once the transport system places one of the storage containers with a requested item in that access drawer. The scanners may be drawer scanners each associated with one of the access drawers in the storage matrix. Each of the drawer scanners may scan identification indicia on items placed in one of the storage containers located within one of the access drawers. The storage and retrieval system may also include sensors each associated with one of the access drawers and/or transport system for detecting storage container content status information, such as detecting the presence of one of the storage containers, detecting whether the one of the storage containers is empty, and detecting if contents are protruding out of the storage container.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 1 is a front perspective view of a prescription storage and retrieval system constructed in accordance with embodiments of the present invention;

FIG. 2 a front perspective view of the prescription storage and retrieval system of FIG. 1, illustrating primary doors thereof in an open position, as well as a storage matrix of compartments and a transport system of the prescription storage and retrieval system;

Figure 1:
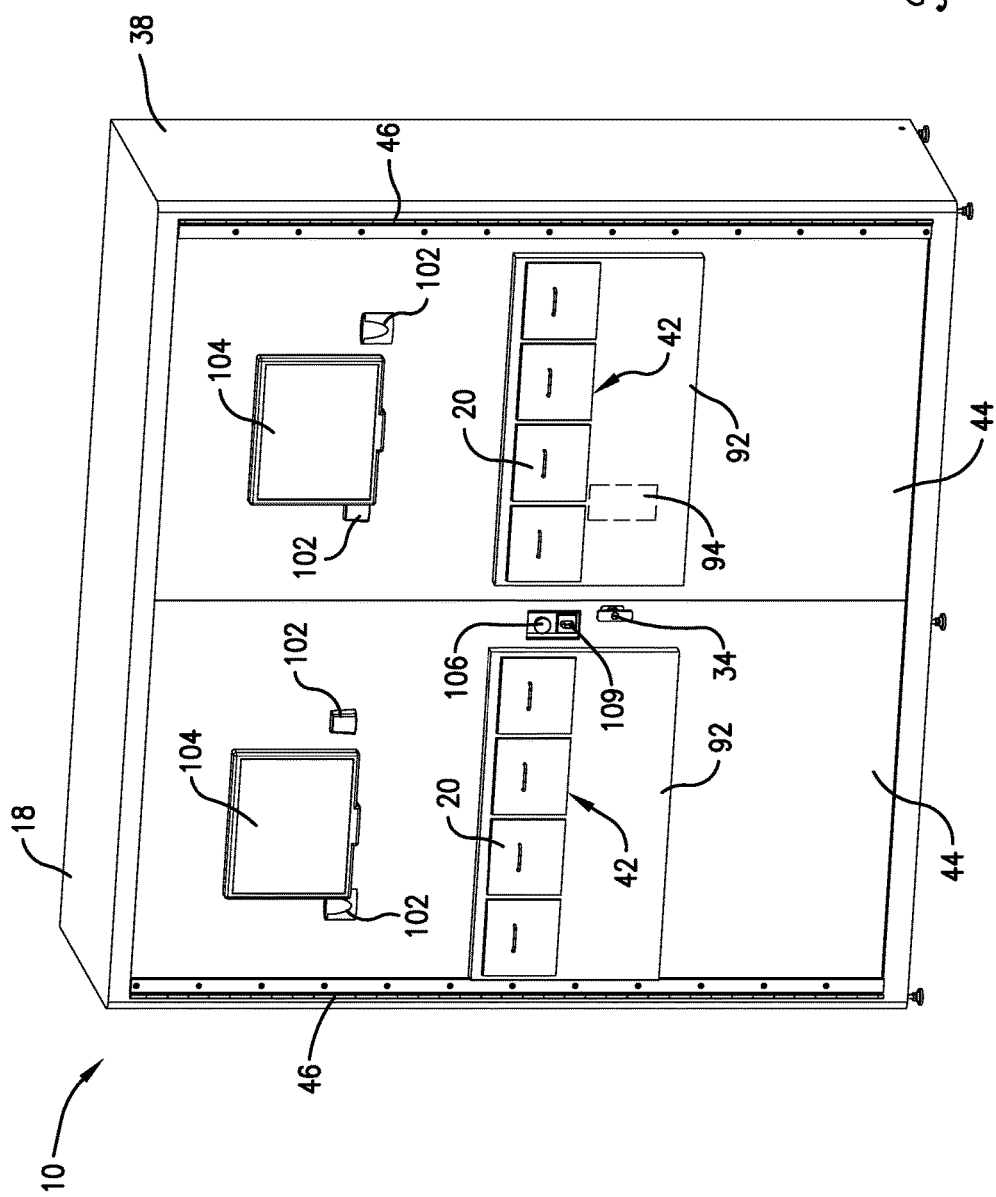

The drawing figures do not limit the present invention to the specific embodiments disclosed and described herein.

The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to one embodiment", an embodiment", or "embodiments" mean that the feature or features being referred to are included in at least one embodiment of the technology. Separate references to one embodiment", an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

The present invention is a system for storing and retrieving physical items with a high degree of accuracy, referencing structural and descriptive metadata contained in external applications related to the items stored. Specifically, some embodiments of the present invention are illustrated in FIGS. 1-31 and include a prescription storage and retrieval system 10 for use in a pharmacy to manage, hold, and safeguard prescriptions 12 or prescription batches 11 filled for pickup by users, patients, or the like. The term "users," as used herein, may refer to patients, customers, or pharmacy staff charged with dispensing the prescriptions to the correct patients or customers. The term "prescriptions," as used herein, may refer to one or more packaged drug items whose distribution is controlled by pharmacists. The prescriptions may be packaged in bags 14, individual prescription bottles, boxes, or the like, and may specifically include prescription batches 11 including one or more different prescriptions for a particular user (such as a particular patient and/or a particular household). In one embodiment of the invention illustrated in FIG. 3, the prescription batches 11 may include the prescriptions 12 and may be individually and/or collectively placed in bags 14 displaying patient labels and identification indicia 16, such as barcodes, QR codes, or the like. The identification indicia 16 may correspond to item, prescription, or prescription batch identification information and other metadata that may be stored in a control system memory or database, as later described herein. For example, a barcode may include a batch number referencing data in a pharmacy dispensing system that controls the prescription filling, bagging, and patient dispensing processes. The metadata may include a person designated to pick up the prescription, details regarding the prescription contents, prescription use instructions, etc.

An embodiment of the prescription storage and retrieval system 10 broadly includes a storage matrix 18, locking devices 32,34,94, access drawers 20, storage containers 22, a transport system 24, scanners 26,28, sensors 30, and a control system 36. Each of these components is described in more detail below.

The storage matrix 18 may comprise an outer housing 38 and a plurality of compartments 40 in the housing. The outer housing 38 may be an enclosure of any shape and configuration and may be made of sheet metal weldment or any sufficiently rigid materials. The outer housing 38 has one or more access openings 42 formed therethrough for retrieval of prescription batches 11 or other stored items by customers and/or pharmacy staff. The outer housing 38 may be, for example, a cabinet having a frame and/or walls and one or more primary doors 44 cooperatively forming an enclosure. In some embodiments of the invention illustrated in FIG. 2, the primary doors 44 may be attached to and/or integral with some or all of the compartments 40 of the storage matrix 18, such that when one of the primary doors 44 is open, the compartments 40 attached thereto also move with the associated primary door 44. The primary doors 44 may be lockable via various ones of the locking devices 32,34, as later described herein. The access openings 42 may be formed through the primary doors 44. Furthermore, the access openings 42 may each be located in the same or different rows and/or columns of the storage matrix without departing from the scope of the invention.

The outer housing 38 may have a physically compact size and shape sufficient to fit in a typical pharmacy and maximize capacity of available storage space. For example, the outer housing 38 may have a substantially planar outer housing configuration, such as a rectangular or cube shape. With the exception of the primary doors 44 and the access openings 42 described above, the outer housing 38 may be substantially closed to user access from its front, bottom, sides, top, and/or back. Specifically, the primary doors 44 and access openings 42 may be situated on the front of the outer housing 38, the compartments 40 may be attached to the primary doors 44, and there may be a space between a back edge of the compartments 40 and a back wall of the outer housing 38 through which the transport system 24 may travel. The open back of the compartments 40 may allow the transport system 24 to retrieve the storage containers 22 therethrough.

In one alternative embodiment of the invention, a space between the compartments 40 and one or more of the sidewalls of the outer housing 38 may be provided to allow the transport system 24 to retrieve the storage containers 22 therethrough. In general, it may be desirable that an open back or side of the compartments 40 be positioned within the outer housing 38 such that access to these compartments 40 of the storage matrix 18 and/or access to the transport system 24 can only be obtained by unlocking one or more of the locking devices 32,34 later described herein.

Figure 2:
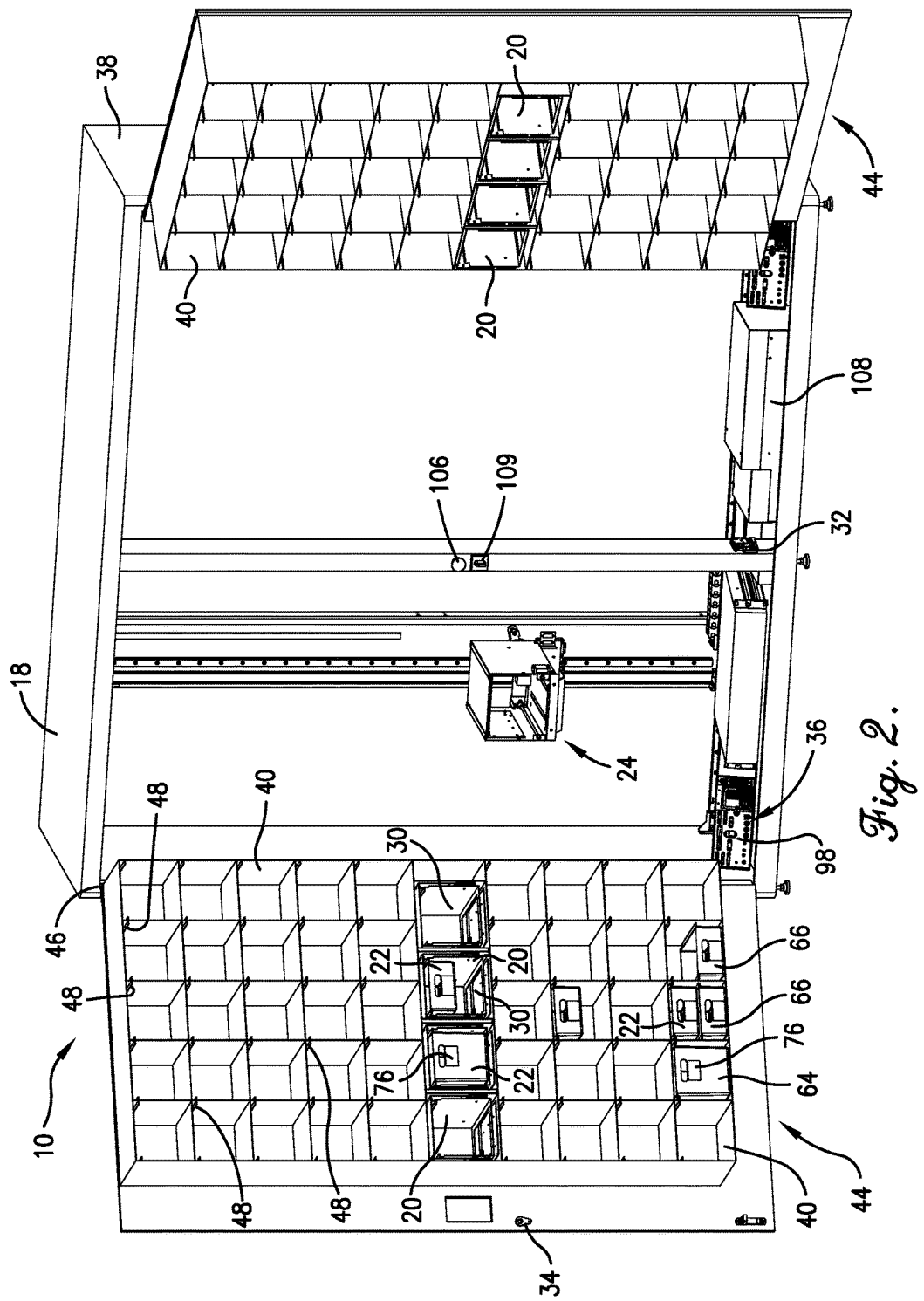
Figure 3:
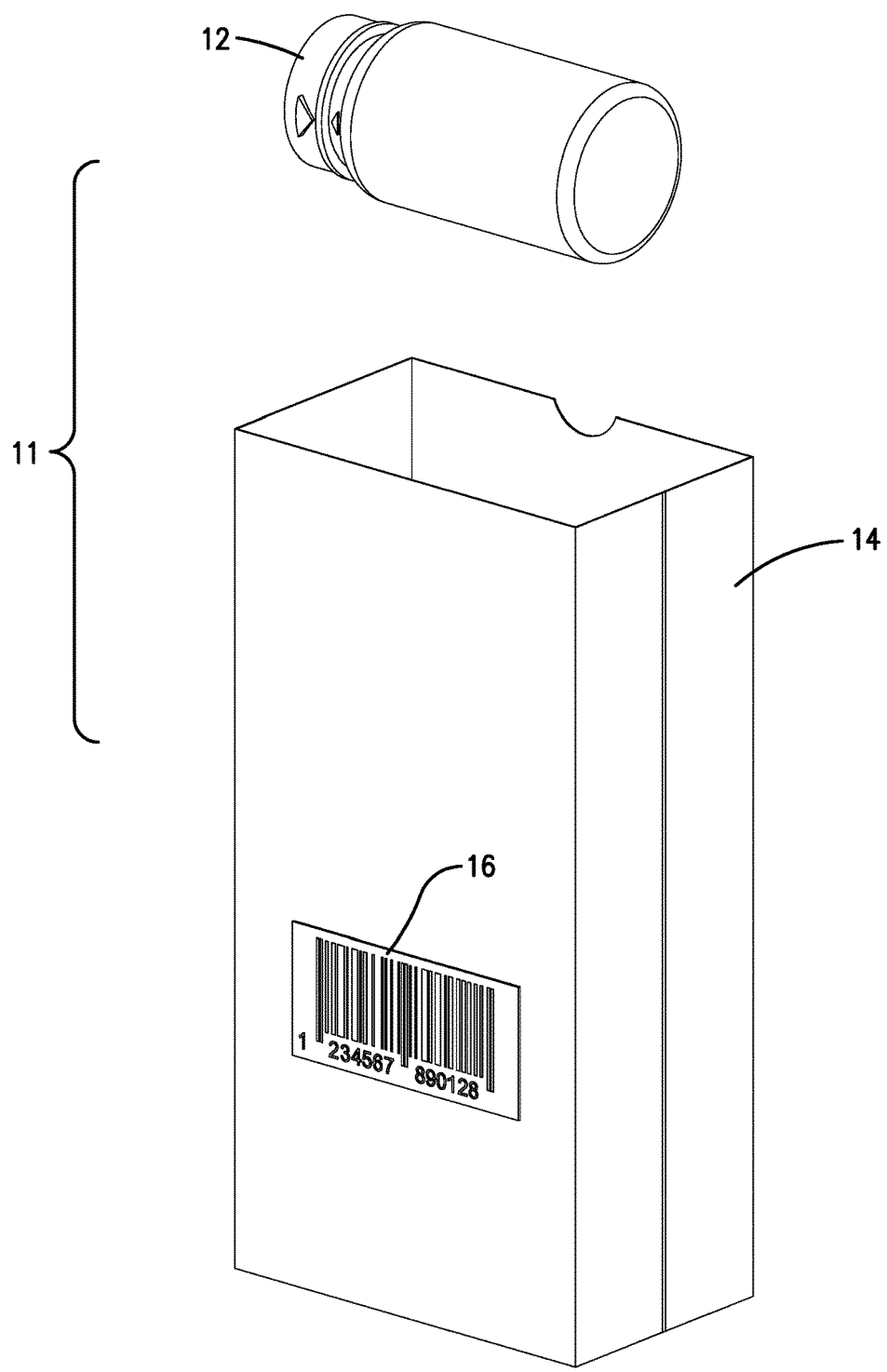
FIG. 3 is a perspective view of a prescription batch, including a prescription, a bag, and identification indicia placed thereon for placement in the prescription storage and retrieval system.

In some embodiments of the invention, portions of the storage matrix 18, such as the primary doors 44, may be rotatably and/or pivotably openable via a hinge mechanism 46 or the like. Specifically, the primary doors 44 and their associated compartments 40 can be moved, rotated, or pivoted about the hinge mechanism 46, allowing a person to open all or part of the storage matrix 18 to gain access to the transport system 24 for servicing. For example, the hinge mechanism 46 may include a four bar linkage or a piano hinge, as illustrated in FIGS. 1 and 2, used to hinge right and left halves of the storage matrix 18, so these halves or primary doors 44 can be pivoted or rotated out of the way to allow service access to the transport system 24, which may be located behind the right and left halves and behind the compartments 40. Shelves, counter space, signs or other useful apparatus may also be attached to the front of the outer housing 38 and/or the primary doors 44 for general use by pharmacy staff, and may also move along with the primary doors 44 when opened and closed to access the transport system 24.

The compartments 40 of the storage matrix 18 may be configured for receiving the storage containers 22. In some embodiments of the invention, the compartments 40 are square or rectangular and arranged in a matrix of columns and rows. Walls of the compartments 40 may have protrusions 48 extending inward therefrom or other structures configured to slidably support the storage containers 22 placed therein. In some embodiments of the invention, the compartments 40 may be sized to house storage containers 22 only a single storage container deep, so no storage container 22 must be moved to get to any other storage container 22. However, in other embodiments of the invention, particularly for use at pharmacies where higher storage density is required, the compartments 40 may be sized and configured to store multiple storage containers 22 longitudinally and the transport system 24 may be capable of moving storage containers 22 in order to allow access to storage containers 22 that are blocked. Additionally or alternatively, the storage matrix 18 may comprise multiple layers of compartments 40, and inner-most layers closest to the transport system 24 may be motorized, for example, by linear motors or lead screws powered by DC motors driven to limit switches. However other methods of moving different layers of compartments 40 may be used without departing from the scope of the invention.

The locking devices 32,34 may be shifted between locked and unlocked configurations for selective access within the outer housing 38 via the primary doors 44, while the locking devices 94 (also referred to herein as "electronic drawer locks 94") may provide selective access to the access drawers 20, as later described herein. In the locked configuration, the locking devices 32,34 may prevent opening of one or more primary doors 44 via pivoting or rotating about the hinge mechanism 46. As illustrated in FIGS. 1, 2, 4, 5, 7, and 15, the locking devices 32,34 may include electronic door locks 32 and/or manual override lock 34. The electronic door locks 32 may normally be electronically operated by a signal from the control system 36, and the control system 36 may receive external power, such as power from a wall outlet or the like. In some embodiments of the invention, the electronic door locks 32 may be solenoid driven. However, any type of electronic locks known in the art may be used as described herein without departing from the scope of the invention.

The manual override lock 34 may be any lock known in the art, configured to be unlocked via a backup key or other manual methods for unlocking a manual lock. In some embodiments of the invention, the manual override lock 34 may be integrated into the electronic door locks 32 or may be a manual override feature of the electronic door locks 32. For example, override of the electronic door locks 32 by a physical key may be available to use in case of external power failure or other failure in the authentication system.

Figure 7:
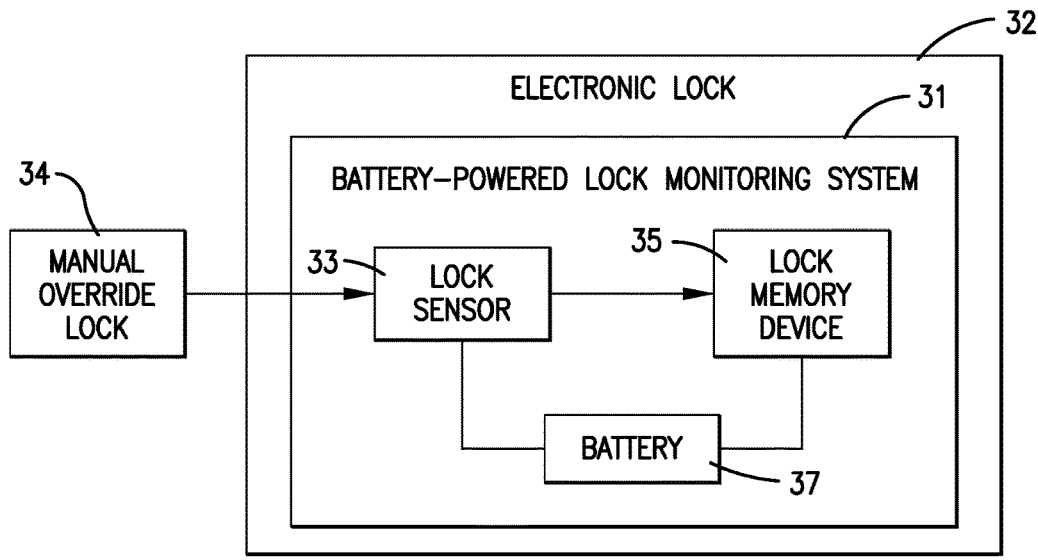
FIG. 7 is a schematic diagram of an electronic door lock for the primary doors of FIG. 2.

In some embodiments of the invention illustrated in FIG. 7, the electronic door locks 32 may include a battery powered lock monitoring system 31 configured to detect and record opening of one or more portions of the storage matrix 18, even when external power is removed from the control system 36, the electronic door locks 32, the transport system 24, the scanners 26,28, and/or the sensors 30. For example, the battery powered lock monitoring system 31 may include one or more lock sensors 33 and a lock memory device 35 both electrically connected to backup battery power 37. The lock memory device 35 may be configured to receive and store an indication from the lock sensors 33 when the manual key is used in the manual override lock 34. Additionally or alternatively, the lock sensor 33 may indicate to the lock memory device 35 when one of the primary doors 44 is actuated to an open position, even when external power is off or removed. Thus, the pharmacy staff or other authorized individuals can be made aware of unauthorized access that occurred during a power outage, as well as a time of when this unauthorized access occurred. In some embodiments of the invention, data stored in the lock memory device 35 may be read or retrieved by the control system 36 after external power is restored thereto.

The access drawers 20 may be located at and at least partially extend through the access openings 42 of the storage matrix 18, opening to provide access to selected prescription batches 11, as illustrated in FIGS. 1, 2, and 4-6, for example. The access drawers 20 allow multiple pharmacy staff members to load prescription batches 11 into the prescription storage and retrieval system 10 simultaneously. In some embodiments of the invention, the access drawers 20 may be slidably arranged on drawer slides 50 or protrusions 48 within one of the access openings 42 and may be configured to slide substantially horizontally into and out of the storage matrix 18.

Each access drawer 20 may include a front wall 52 having a handle 54 or other handle-like portion configured to be pulled by a user opening the access drawer 20. Each access drawer 20 may also include two side walls 56 having components of the drawer slides 50 fixedly or movably attached thereto, such as tracks, wheels, ball bearings, or the like coupled to outer surfaces of the side walls 56, configured to slidably interface with other components of the drawer slides 50, such as corresponding tracks, rails, or other such features fixed within the access openings 42 into which the access drawers 20 are slid. Each access drawer 20 may also include ledges or other such protrusions onto which flanges or other portions of the storage containers 22 may be placed. This may allow the access drawers 20 to support the storage containers 22 without the use of a bottom wall.

Specifically, in some embodiments of the invention, the access drawers 20 may not have bottom walls and/or may have bottom walls 60 with one or more openings 62 formed therethrough, allowing for direct scanning of identification indicia 16 on the prescription batches 11 placed face-down in a storage container 22, as later described herein. In still other embodiments of the invention, the access drawers 20 may each include a bottom wall that may be formed of transparent material. Additionally or alternatively, the front and side walls may be formed of transparent material. The transparent material allows the scanners 26,28 and/or sensors 30 to obtain data regarding a prescription batch 11 and/or a storage container 22 therethrough. The access drawers 20 may also each be designed with a substantially open back and an open top thereof, allowing retrieval of the storage containers 22 through the open back via the transport system 24 located rearward of the access drawers 20 and/or allowing retrieval of the storage containers 22 by opening the access drawer 20 and reaching down through the open top thereof.

Figure 6:
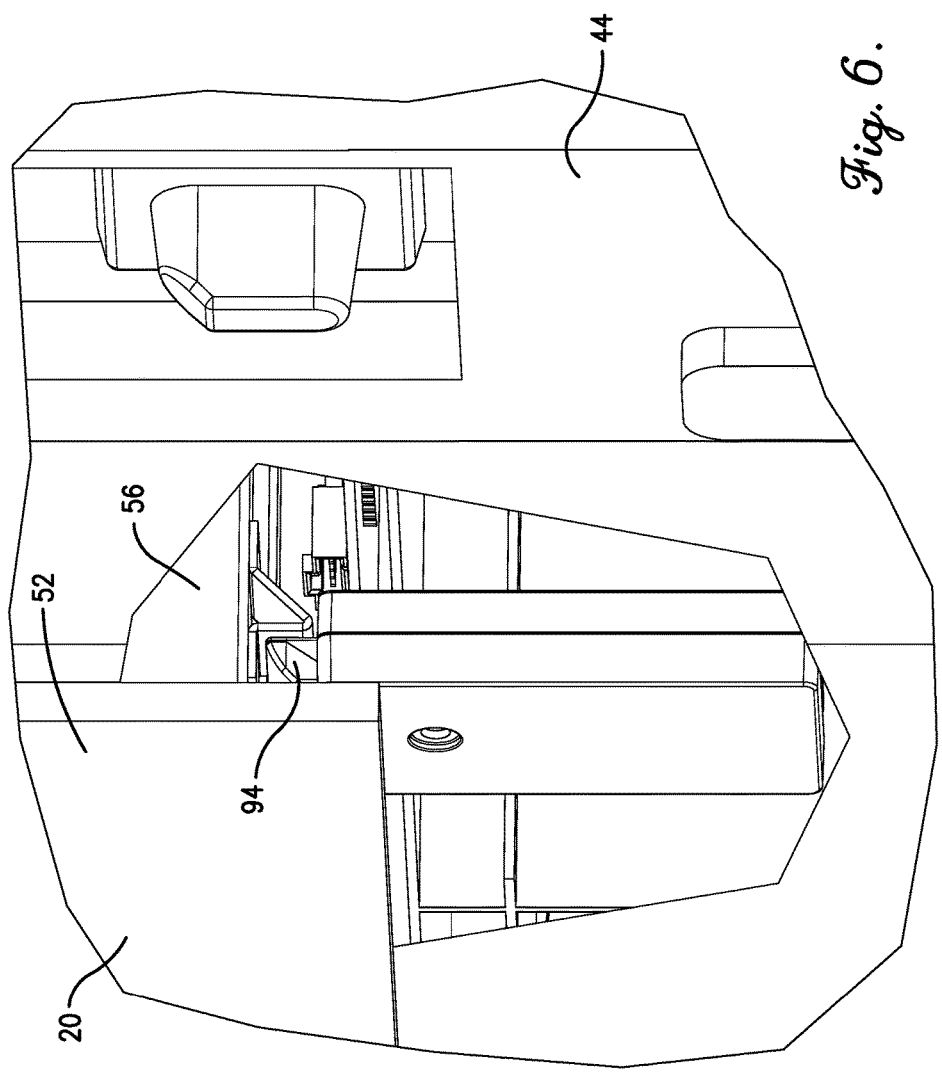
FIG. 6 is a fragmentary front perspective view of the outer housing and one of the drawers of FIG. 5, with a portion of the outer housing broken away to reveal an electronic drawer lock for selectively locking the drawer in a closed position.

As illustrated in FIG. 6, each of the access drawers 20 may have one of the electronic drawer locks 94 automatically engaging or locking when the access drawer 20 is shut, and being electronically released via commands from the control system 36. For example, the electronic drawer lock 94 may be an electronic apparatus having a rigid latch portion that extends in front of the access drawer 20 to prevent withdrawal thereof, but that is operable to slide, rotate, or otherwise moved out of the way of the access drawer 20 to allow the access drawer 20 to be pulled open in an outward direction at least partially through the access opening 42. The access drawers 20 may also each include and/or engage with a resilient member (not shown), such as a spring configured to push the access drawer slightly open when the access drawer 20 is unlocked and/or unlatched.

In alternative embodiments of the invention, one or more of the access drawers 20 may be omitted or other mechanisms for providing access to the prescriptions may be used instead of the access drawers 20. For example, in addition to or in place of the access drawers 20, access doors or the like may be used to selectively provide access, via the access openings 42, to an associated one of the compartments 40 covered thereby. The access doors may be configured for sliding open, pivoting about a hinge or the like, being temporarily detached from the storage matrix, or any other method known in the art for opening a door, cover, lid, or the like. Latches as described above and/or locking devices, such as the electronic locks described herein, may prevent unauthorized opening of the access doors.

Figure 9:
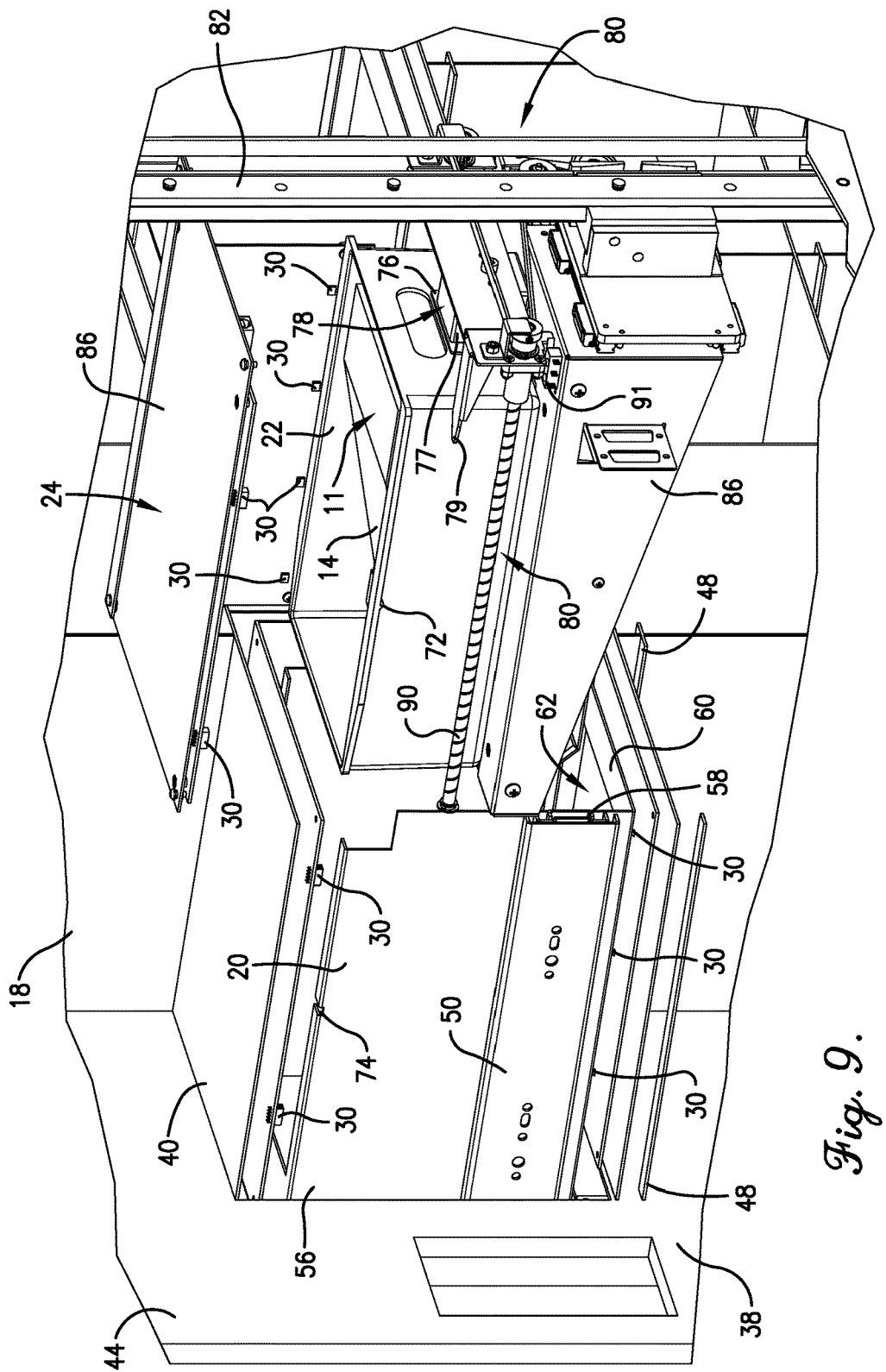
FIG. 9 is a fragmentary side perspective view of the transport system and one of the drawers of FIG. 5 with portions of the storage matrix removed, illustrating the transport system in a retracted configuration for carrying a storage container holding the prescription batch to another location within the storage matrix and/or for transporting the storage container back to one of the drawers.
Figure 10:
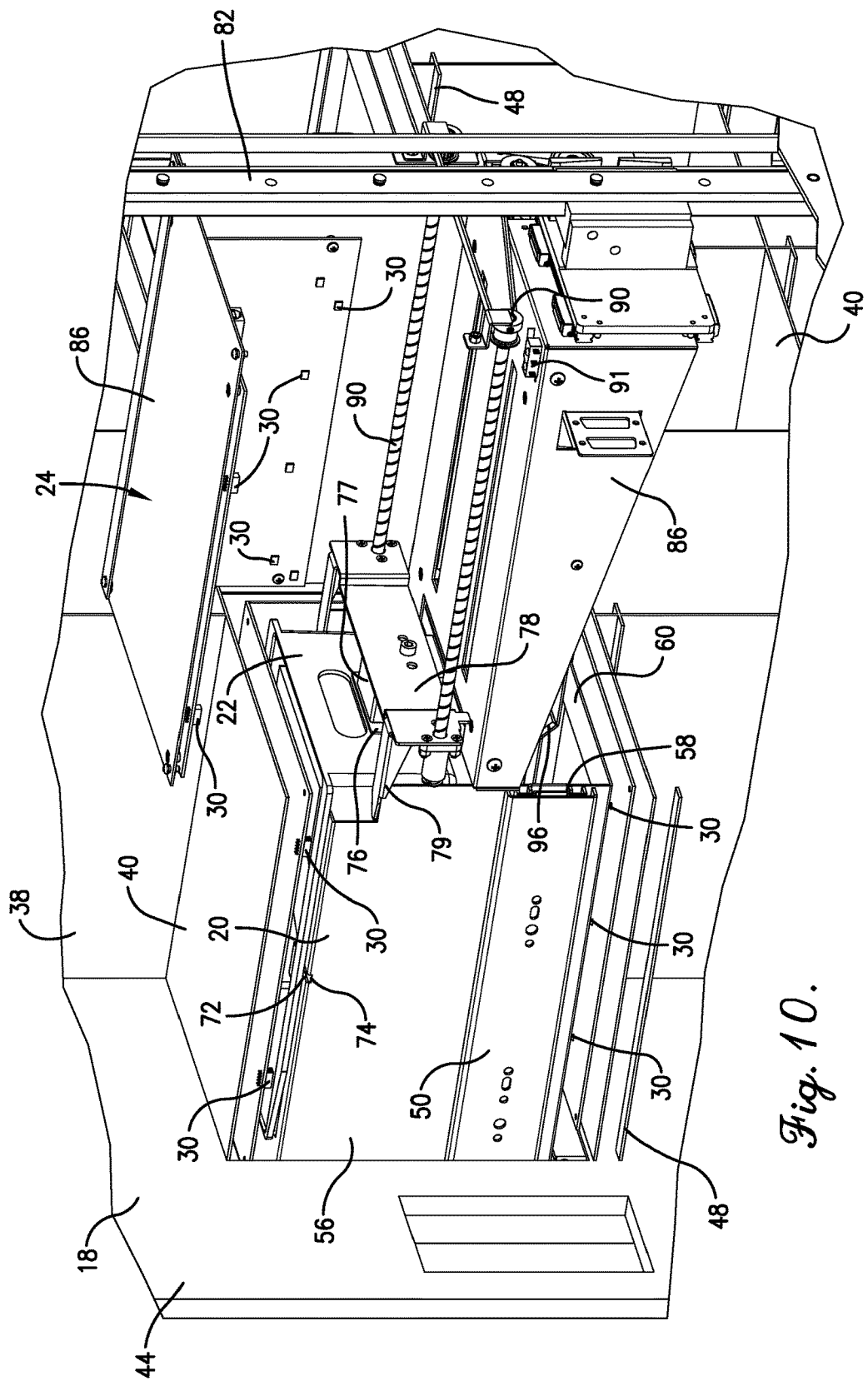
FIG. 10 is a fragmentary side perspective view of the drawer of FIG. 9, illustrating the transport system in an extended configuration to retrieve the storage container from and/or dispense the storage container into the drawer.

The storage containers 22, as illustrated in FIGS. 2, 9, and 10, for example, are configured to receive and hold standard pharmacy bags for temporarily holding one or more prescriptions or items for patient pickup. The storage containers 22 may be any size and shape and made of any suitable materials. The storage containers 22, constructed in accordance with an embodiment of the present invention, may each be a substantially square or rectangular-shaped container and may have a plurality of sidewalls and a bottom wall. The storage containers 22 may be open or partially open at tops thereof, to allow users to place or remove prescription batches 11 therefrom. Additionally or alternatively, one of the sidewalls or the bottom wall of the storage containers 22 may be mechanically openable or otherwise removable during retrieval of the prescription batches 11 therein.

The storage containers 22 are sized fit into the compartments 40 of the storage matrix 18 and may be moved between various ones of the compartments 40 and/or the access drawers 20 via the transport system 24, as later described herein. However, other sizes, shapes, and configurations of storage containers 22 may be used without departing from the scope of the invention. For example, the storage containers 22 may be sized and shaped to allow the prescription batches 11 therein to be stored longitudinally in the storage containers 22. In some embodiments of the invention, multiple different sizes of storage containers 22 may be housed within the storage matrix 18 compartments. For example, there may be two different sizes of storage containers 22 which may differ in height—a large-sized storage container 64 and a small-sized storage container 66 that is approximately half the height of the large-sized storage container 64, as illustrated in FIG. 2. In some embodiments of the invention, only specific technicians or users may be authorized to remove the storage containers 66,64, and may manage the storage container supply by placing the storage containers 22 of appropriate sizes into access drawers 20 or by removing them from the access drawers 20. This may be done to initially load the storage containers 22 into desired configurations, replace defective storage containers 22, and/ or optimize a balance between large-sized storage containers 64 and small-sized storage containers 66.

Figure 5:
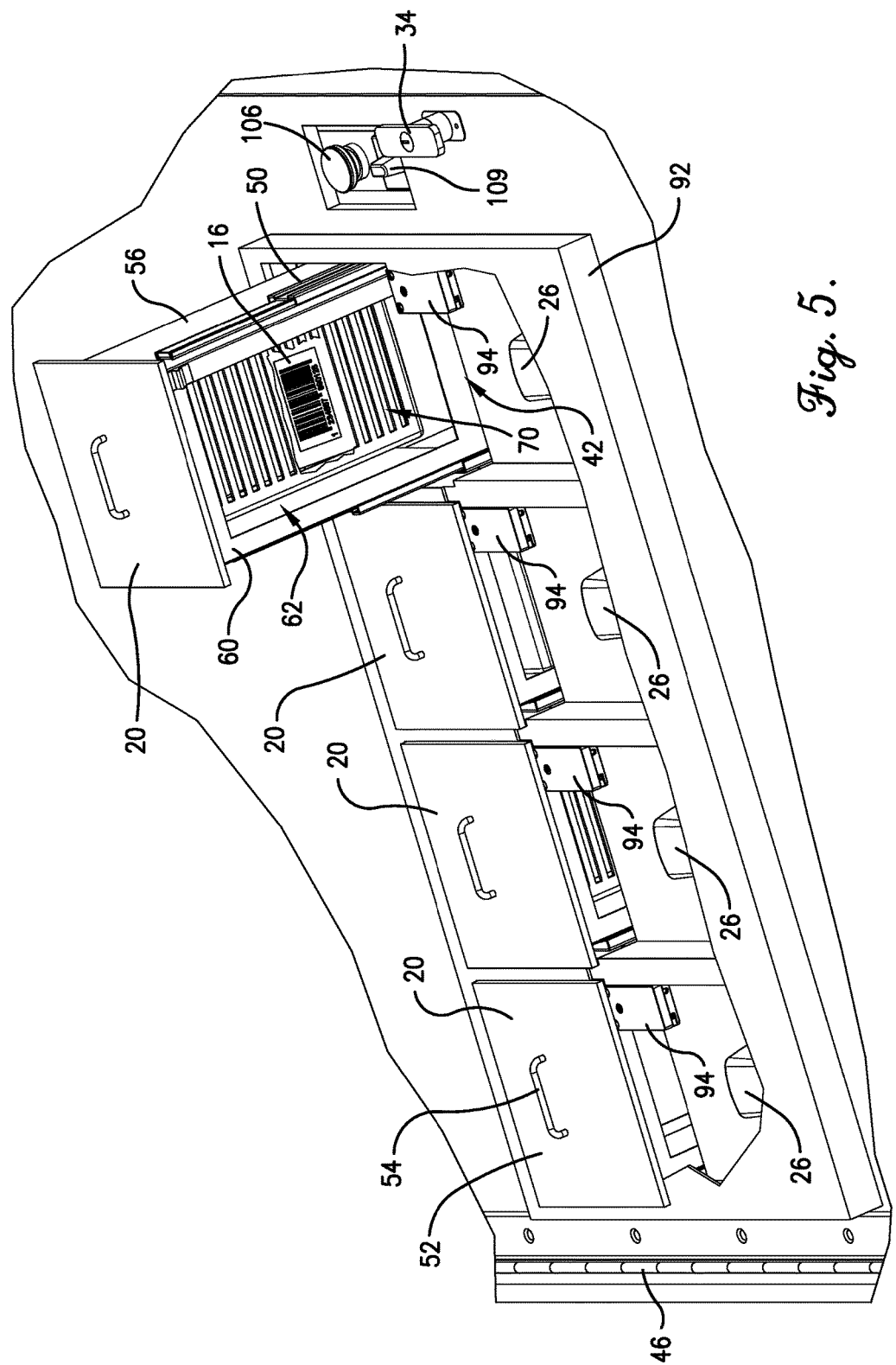
FIG. 5 is a fragmentary bottom front perspective view of the outer housing, drawers, and scanners of the prescription storage and retrieval system of FIG.

In some embodiments of the invention, the storage containers 22 may include flanges 68 configured for engaging with tracks or other alignment devices within the compartments 40 and/or within the access drawers 20. At least a portion of the flanges 68 may be chamfered at one or both ends to allow easier alignment with the tracks or other alignment devices within the compartments 40, assisting in overcoming any slight misalignments that would otherwise cause some interference. As illustrated in FIG. 5, the bottom wall of the storage container 22 may have a plurality of slots 70 or openings formed therethrough, allowing any one of the scanners 26,28 to scan a barcode, QR code, or other identification indicia 16 from the prescription batches 11 placed face-down into the storage containers 22.

Figure 12:
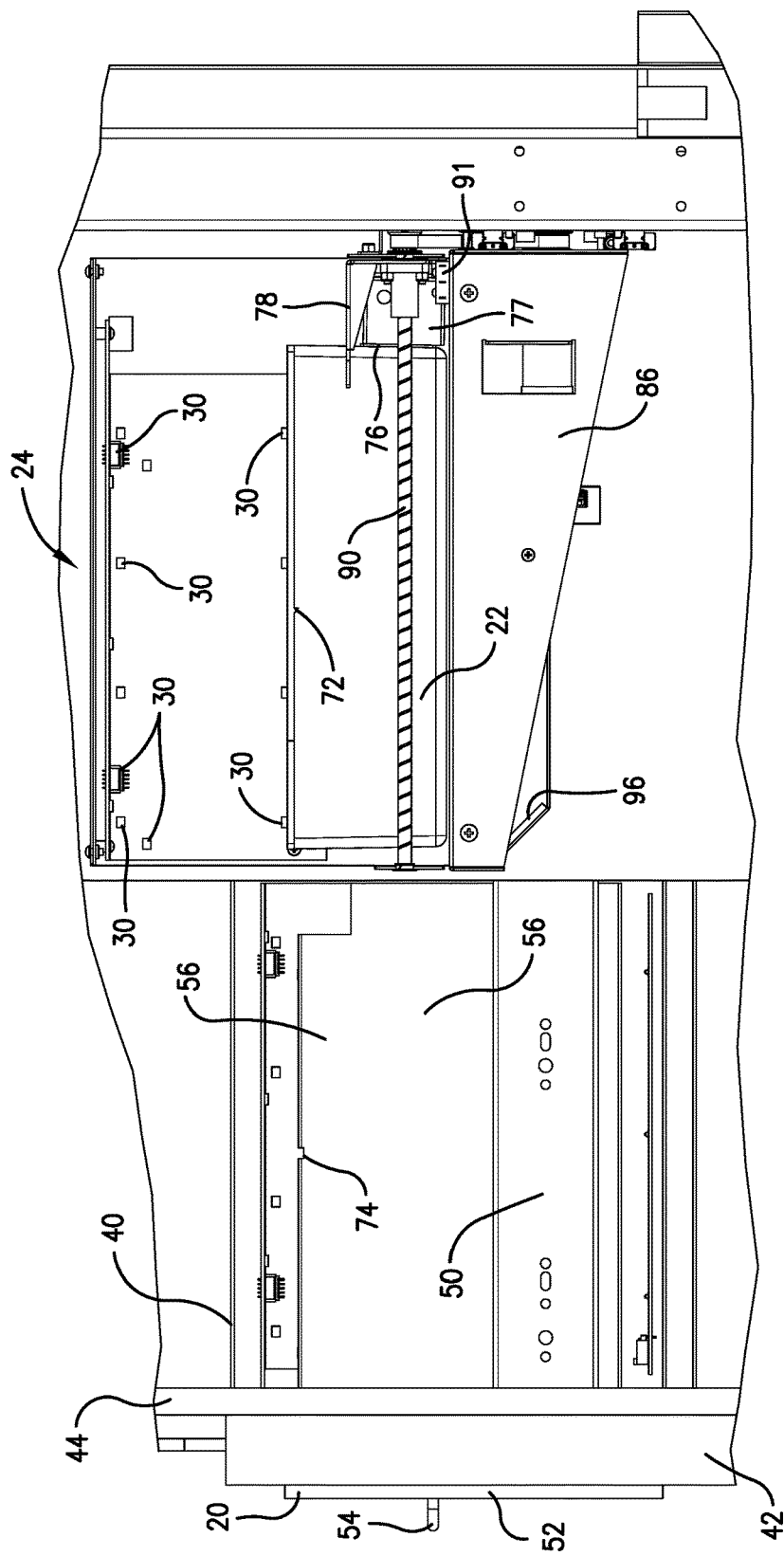
FIG. 12 is a fragmentary side view of the drawer and transport system of FIG. 9 with the transport system trolley aligning the storage container thereon with the drawer.
Figure 13:
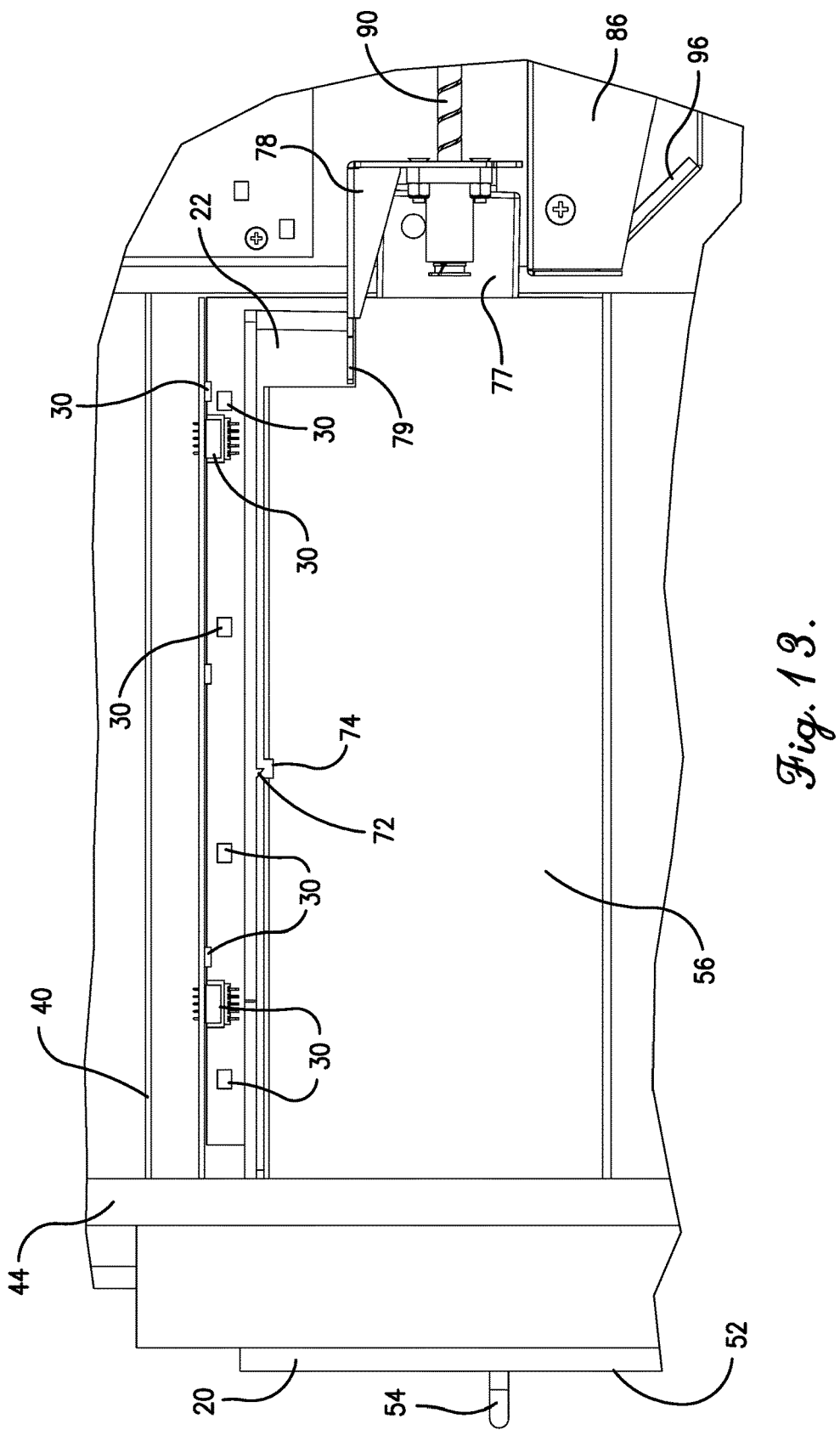
FIG. 13 is a fragmentary side view of the trolley and the drawer of FIG. 12, with the storage container pushed into the drawer and elements of the transport system located in the extended configuration.
Figure 14:
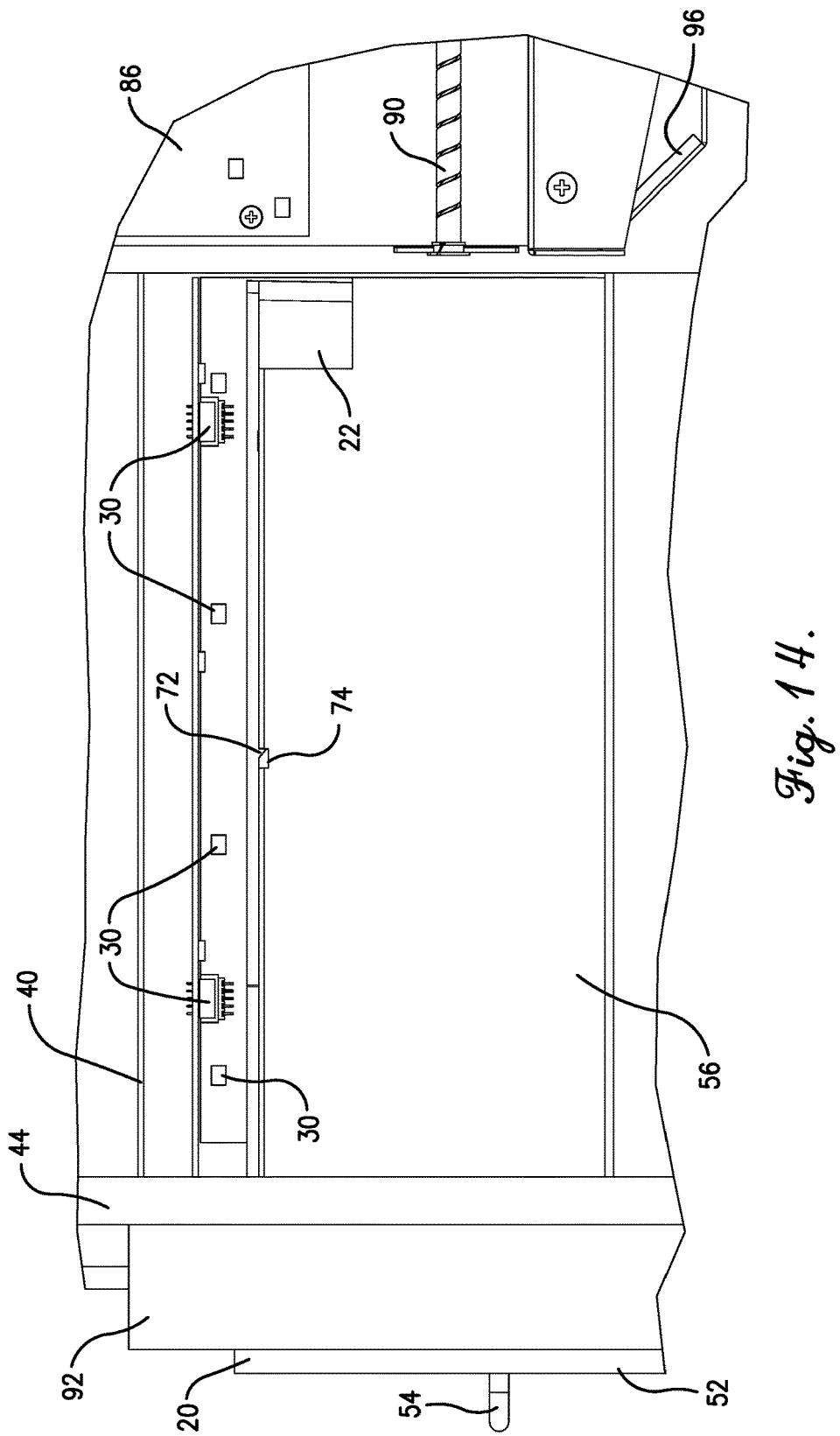
FIG. 14 is a fragmentary side view of the trolley and the drawer of FIG. 13, with the storage container resting within the drawer and elements of the transport system located in the retracted configuration.

In some embodiments of the invention, as illustrated in FIGS. 12-14, the storage containers 22 may also include a tooth 72, protrusion, ledge, or other feature preventing the storage containers 22 from being fully withdrawn through the access openings 42 during prescription retrieval. For example, the storage containers 22 may have at least one tooth 72 configured to engage a notch 74 in the access drawers 20, preventing forwards and/or upwards withdrawal of the storage containers 22 by the user. By preventing the storage containers 22 from being fully removed from the storage matrix 18, clutter can advantageously be avoided and pharmacy workflow simplified.

Additionally or alternatively, two levels of electronically activated cams may be used to retain the access drawers 20 and/or to alternately prevent and allow removal of the storage containers 22 from the access drawers 20 by a technical user or other authorized user. For example, a first level of cams may be configured to allow the access drawers 20 to open far enough for a typical user to store or retrieve an item from the storage containers 22 in the access drawers 20. A second level of cams may be configured to allow a technical user to remove the storage containers 22 or enter a new storage container 22 into the access drawers 20.

The storage containers 22 may include features enabling them to be positively gripped by the transport system 24. In some embodiments of the invention, as illustrated in FIGS. 9 and 10, at least one attachment portion 76, such as a metal plate, a magnet, a conductive surface, or the like, may be integrated into and/or attached to the storage containers 22. The storage containers 22 may be manipulated by, attached to, and/or relocated by the transport system 24 via the attachment portion 76. For example, in some embodiments of the invention, the attachment portion 76 is a metal plate fixed to one end of the storage containers 22 and is configured to attach to an electromagnet of the transport system 24, as later described herein.

Figure 29:
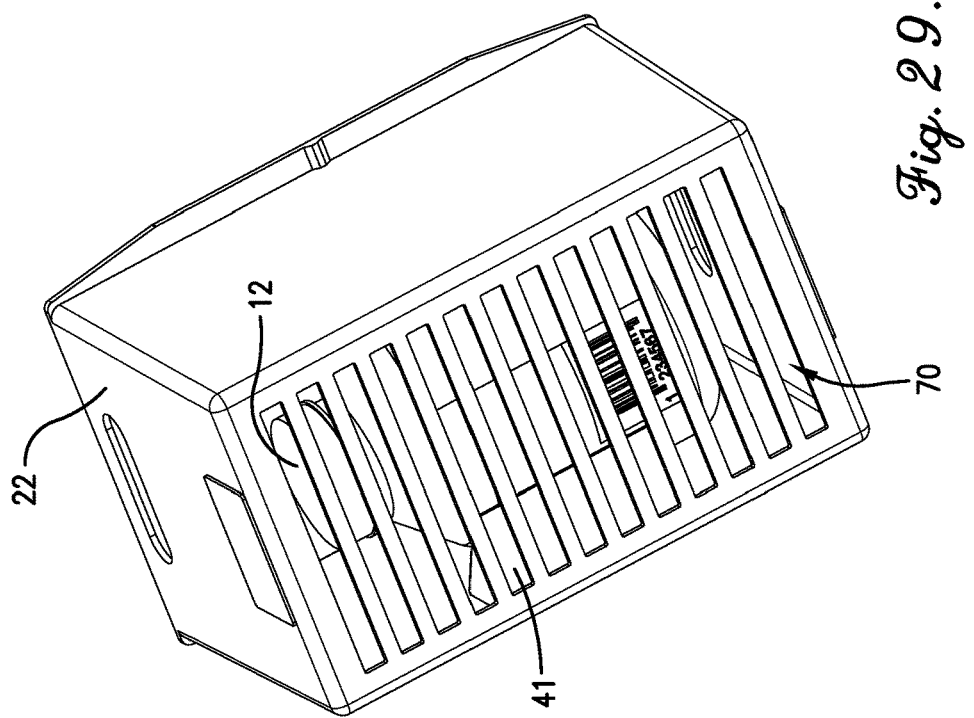
FIG. 29 is a bottom perspective view of the storage container including the insert.
Figure 28:
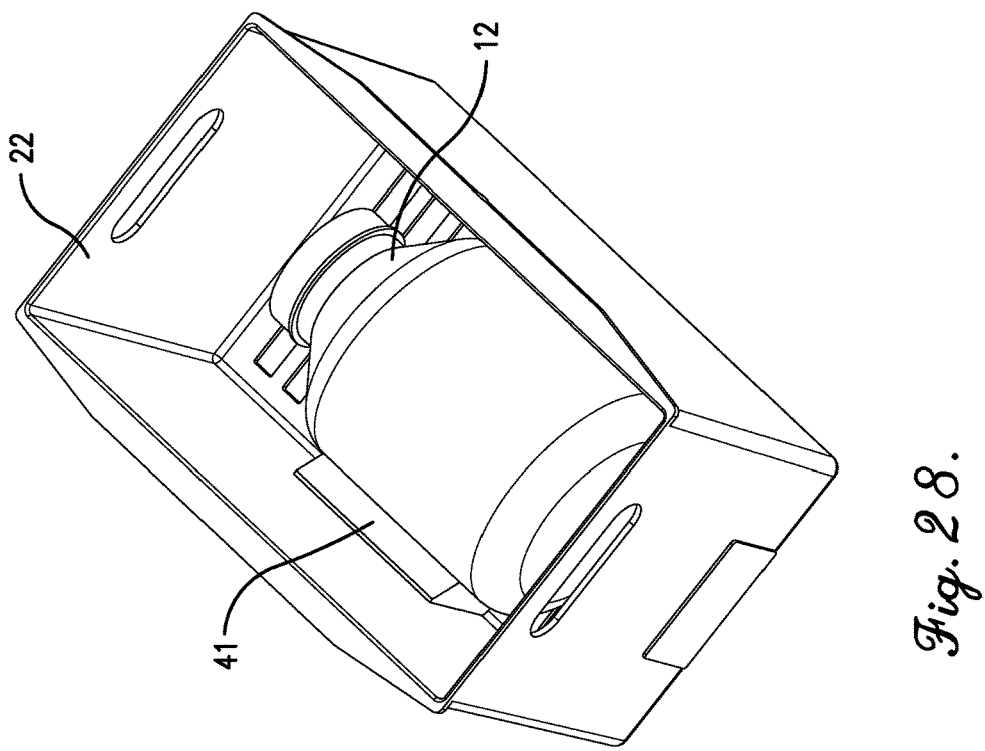
FIG. 28 is a top perspective view of one of the storage containers including an insert for holding an item in place.

Furthermore, in some embodiments of the invention, the storage containers 22 may be configured for individual stock bottles or drug packages, and may thus comprise various inserts configured for maintaining the bottles or packages in a correct orientation in order to read or scan identification indicia 16 thereon as the access drawer 20 is closed. For example, an insert 41 may be installed in a front of one of the storage containers 22, as illustrated in FIGS. 28-29. There may be several types of inserts to cover various configurations of bottles. A bottle, such as prescription 12, may be placed in the insert 41 and the insert 41 may hold it securely in the storage container 22 as the access drawer 20 is closed. There may be one or more bottles held by the insert 41 and/or other bottles loose in the storage container 22, with all bottles in the storage container 22 holding the same drug. The items in the inserts may be tracked by lot number and/or expiration date, plus any other tracking codes or indicia required, via the scanners 26,28 and control system 36, as later described herein.

The transport system 24 is provided for retrieving and transporting the storage containers 22 within the storage matrix 18, and may incorporate any mechanisms capable of selectively attaching to the storage containers 22 and/or actuating movement of the storage containers 22 from one compartment 40 to another. An embodiment of the transport system 24 is illustrated in FIGS. 2, and 8-22, and includes an attachment device 78 and a plurality of actuators 80 configured for supporting and moving the attachment device 78 to different ones of the compartments 40 and/or the access drawers 20 for dropping off and picking up different ones of the storage containers 22.

The attachment device 78, as illustrated in FIGS. 9-14 and 19-23, may be configured to be electrically, magnetically, mechanically, and/or hydraulically activated to attach to and unattach from the storage containers 22 or the attachment portion 76 of the storage containers 22. Specifically, the attachment device 78 may include an electromagnet 77 which may grip the storage containers 22 by attracting a metal plate on one of the storage containers 22 when powered on and releasing the metal plate when powered off. Powering on and off the electromagnet 77 may be accomplished via electronic signals and/or power received via electrical connection to the control system 36, as later described herein. Alternatively, the attachment device 78 may include a motor driven clamp (not shown) that grabs a small protrusion of the storage container 22 or any other features on the storage containers 22 enabling them to be positively gripped by the transport system 24. In some embodiments of the invention, the attachment device 78 may also include mechanical guides 79 at opposing sides of the electromagnet 77 or the like. The mechanical guides may be protrusions configured to stabilize the storage containers 22 attached to the attachment device 78 and assist with side-to-side alignment thereof when the storage containers 22 are being deposited by the transport system 24 into one of the access drawers 20 and/or compartments 40.

Figure 15:
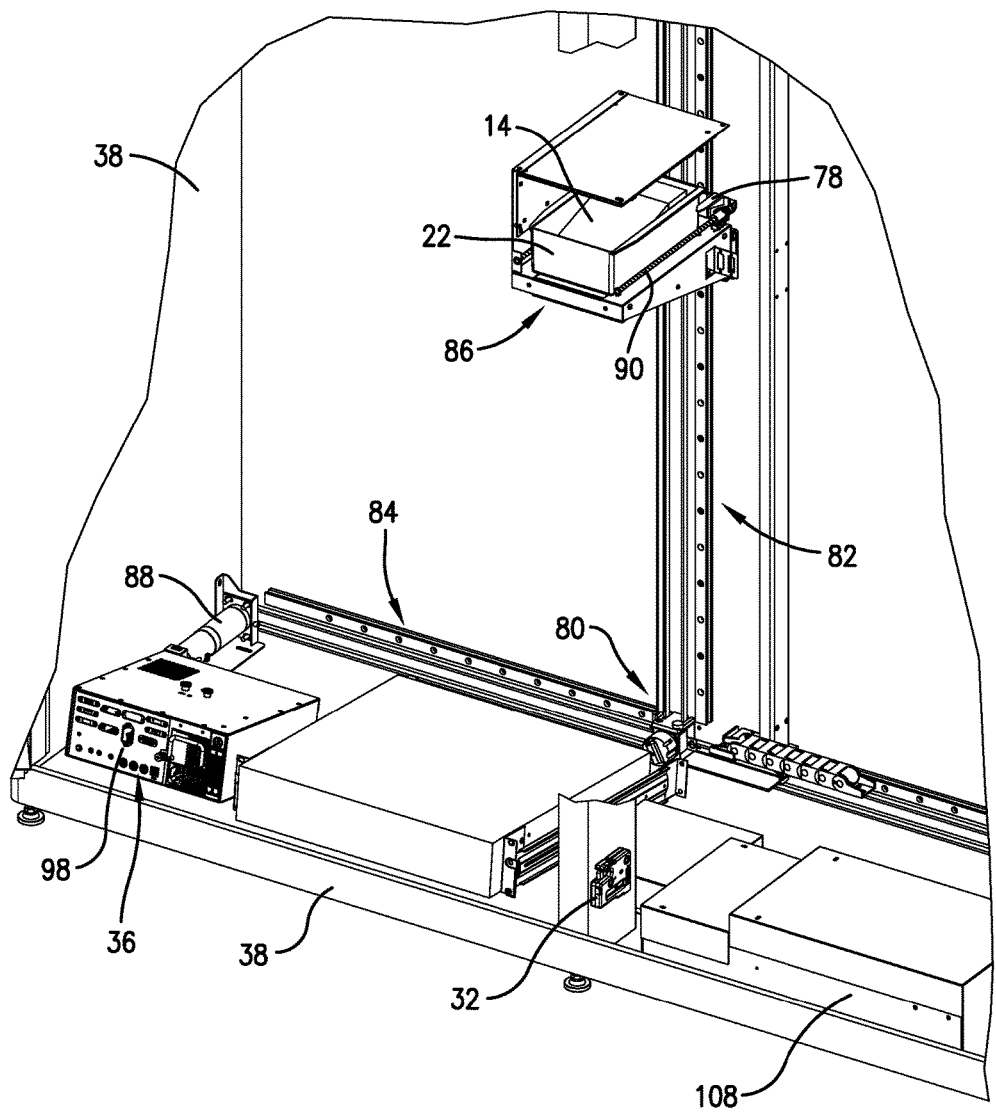
FIG. 15 is a fragmentary front perspective view of the transport system and a control system of the prescription storage and retrieval system of FIG. 2, illustrating bottom horizontal tracks and vertical tracks of the transport system.
Figure 16:
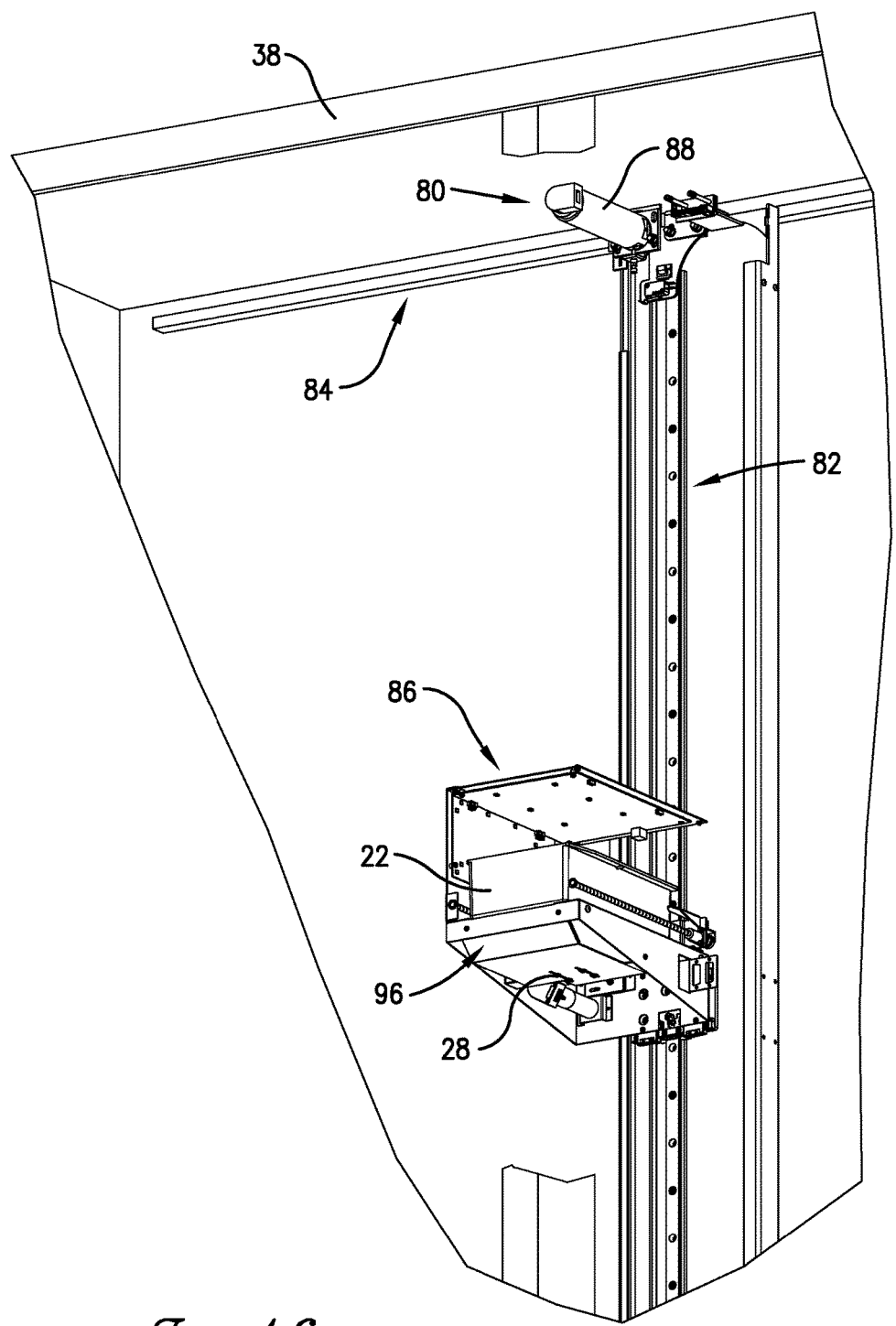
FIG. 16 is a fragmentary front perspective view of the transport system and the control system of FIG. 15, illustrating top horizontal tracks and vertical tracks of the transport system.
Figure 17:
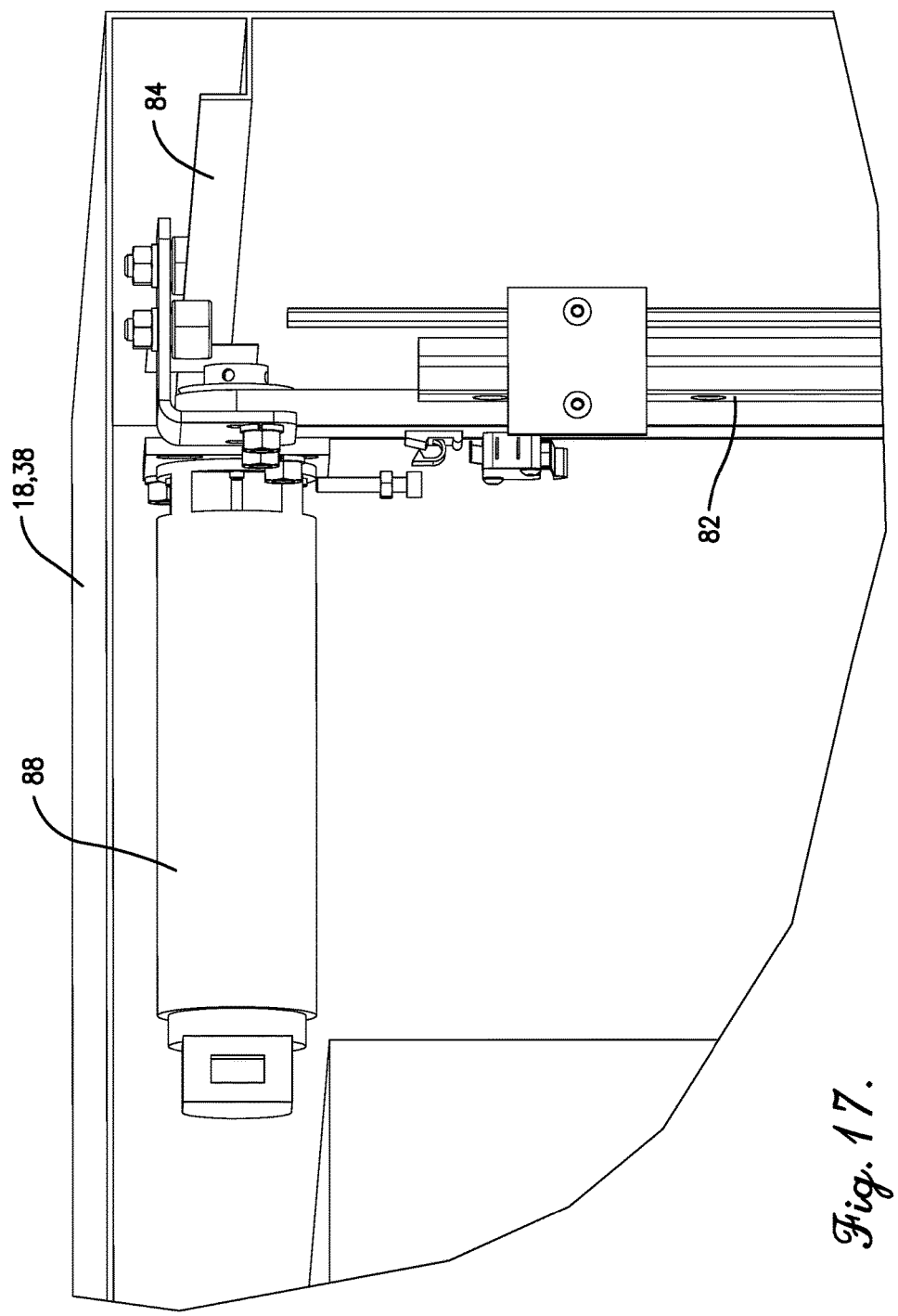
FIG. 17 is a close-up fragmentary side perspective view of the top horizontal track of FIG. 16, illustrating a servo motor of the transport system and rollers, associated with the vertical track, cooperatively rolling along the top horizontal track.

As illustrated in FIGS. 2, and 9-23, the actuators 80 may include a first and second set of vertical and/or horizontal tracks 82,84, a trolley 86 with the attachment device 78 fixed thereto or integral therewith, and one or more motors 88 or drives that actuate the trolley 86 along the first set of tracks 82 and to actuate the first set of tracks 82 linearly along the second set of tracks 84. For example, the trolley 86 may be mounted on a vertical axis track that moves horizontally back and forth along a horizontal track extending a width of the storage matrix 18, as illustrated in FIGS. 15 and 16. Both the tracks 82,84 and the trolley 86 may use motors 88 such as servo motors and/or belt drives to control motion thereof. In one embodiment of the invention, the actuators 80 may include a pick and place drive and a fixed linear drive, and the pick and place drive may move the attachment device 78 along the fixed linear drive. In some embodiments of the invention, the transport system 24 may be a gantry system which moves the attachment device 78 or gripper mechanism through a length and height of the storage matrix 18. For example, motion in the direction of the length and height may be accomplished with the one or more actuators 80, such as a servo motor and belt drive similar to ScriptPro's SPx00 robots made by ScriptPro LLC of Mission, Kans.

Figure 11:
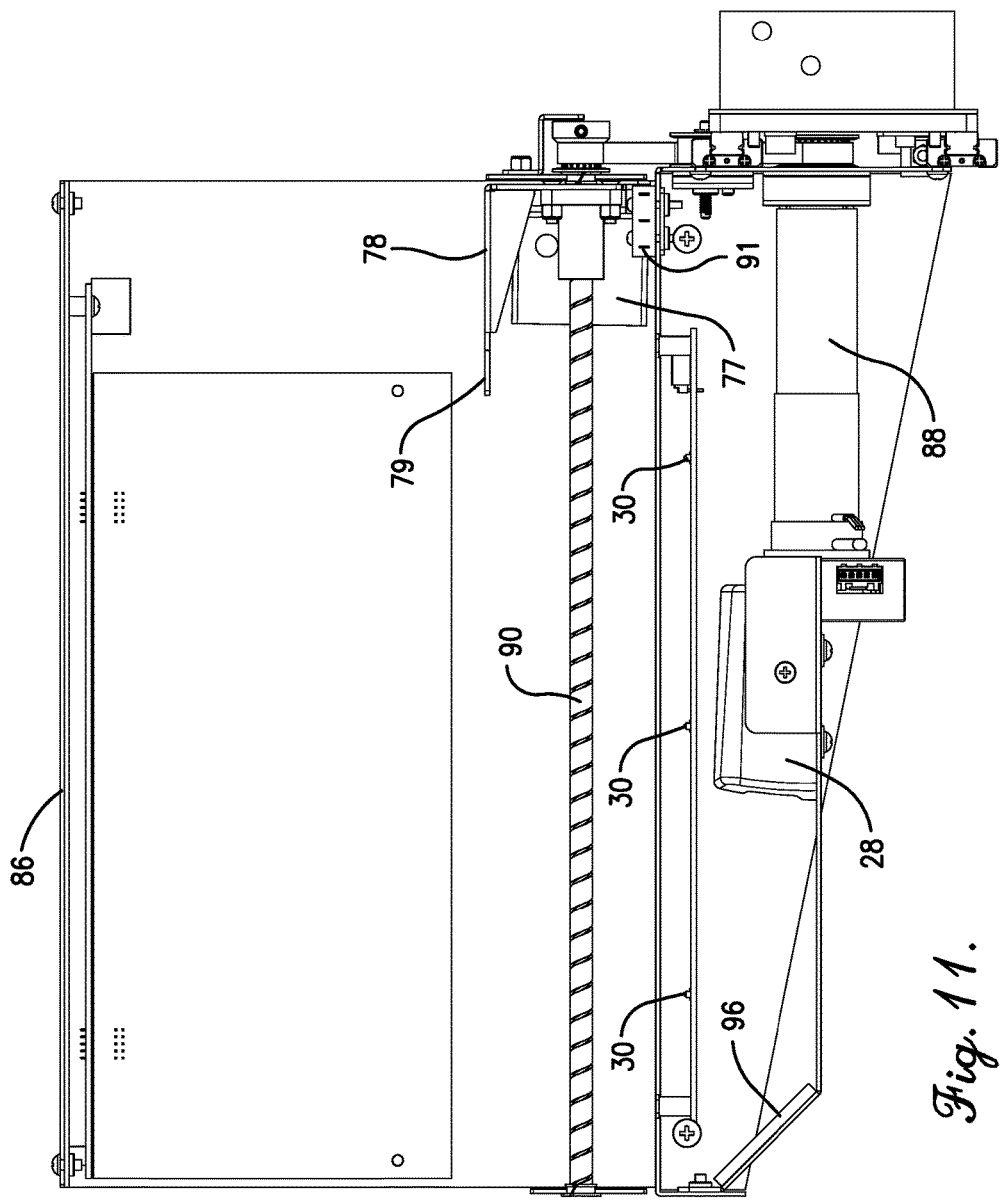
FIG. 11 is a side view of a trolley of the transport system of FIG. 9.

In some embodiments of the invention, the actuators 80 may include a scissor or telescoping mechanism or drive screws 90, as illustrated in FIGS. 9-11, attached to the attachment device 78 for extending and retracting the attachment device 78. For example, the attachment device 78 may include drive screws 90 that are tied to the electromagnet and/or the clamp by a belt and driven by the motor 88, and the drive screws 90 may be configured to move toward and away from the front of the storage matrix 18. This allows the attachment device 78 to reach into one of the compartments 40 or access drawers 20, as needed, and to pull one of the storage containers 22 rearward and out of one of the compartments 40 or access drawers 20 and/or into the trolley 86. Stop switches 91 or limit switches mounted in the trolley 86 and/or on the attachment device 78 may also be communicably coupled with the drive screws 90 and/or controllers thereof to ensure that the storage containers 22 are placed at a desired location within the trolley 86. In some embodiments of the invention, the attachment device 78 may also be mounted on a simple rotating joint that allows 180 degrees of rotation of orientation, so the attachment device 78 can reach storage containers 22 to either side or in front of the scissor or telescoping mechanism.

Figure 4:
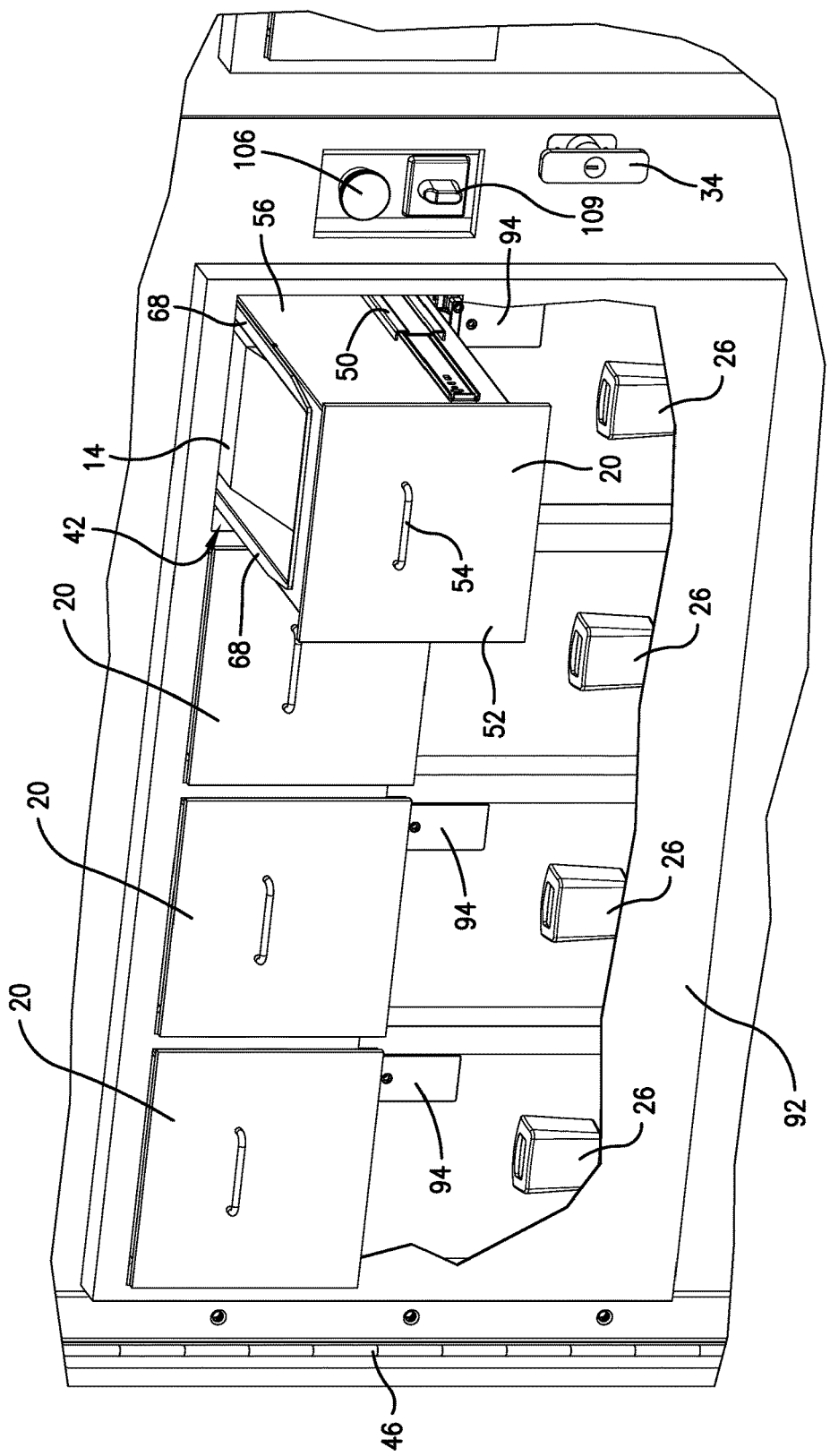
FIG. 4 is a fragmentary front perspective view of an outer housing, drawers, and scanners of the prescription storage and retrieval system of FIG. 1, with a portion of the outer housing broken away.

The scanners 26,28 illustrated in FIGS. 4, 5, and 11 are provided for detecting identification indicia 16 on items placed into the storage matrix 18 and may include one or more indicia readers communicably coupled with the control system 36 via wired or wireless connections. Specifically, the scanners 26,28 may include barcode scanners, smart card readers, QR code readers, RFID tag readers, biometric readers, or the like. In some embodiments of the invention, one or more scanners, referred to herein as drawer scanners 26, may be affixed to the front of the storage matrix 18 and directed substantially upward and/or directed at a mirror which is substantially directed toward the prescription batches 11 in the storage containers 22, as illustrated in FIGS. 4 and 5. For example, the drawer scanners 26 may include an upward facing barcode scanner for each access drawer 20 that reads barcodes on bags 14 and/or prescription batches 11 within the storage containers 22 as the access drawers 20 are closed and/or as the access drawers 20 are opened. Each of the drawer scanners 26 may be associated by the control system 36 with a particular drawer location and/or a particular access opening location, to assist in tracking and transport commands by the control system 36, as later described herein.

Figure 31:
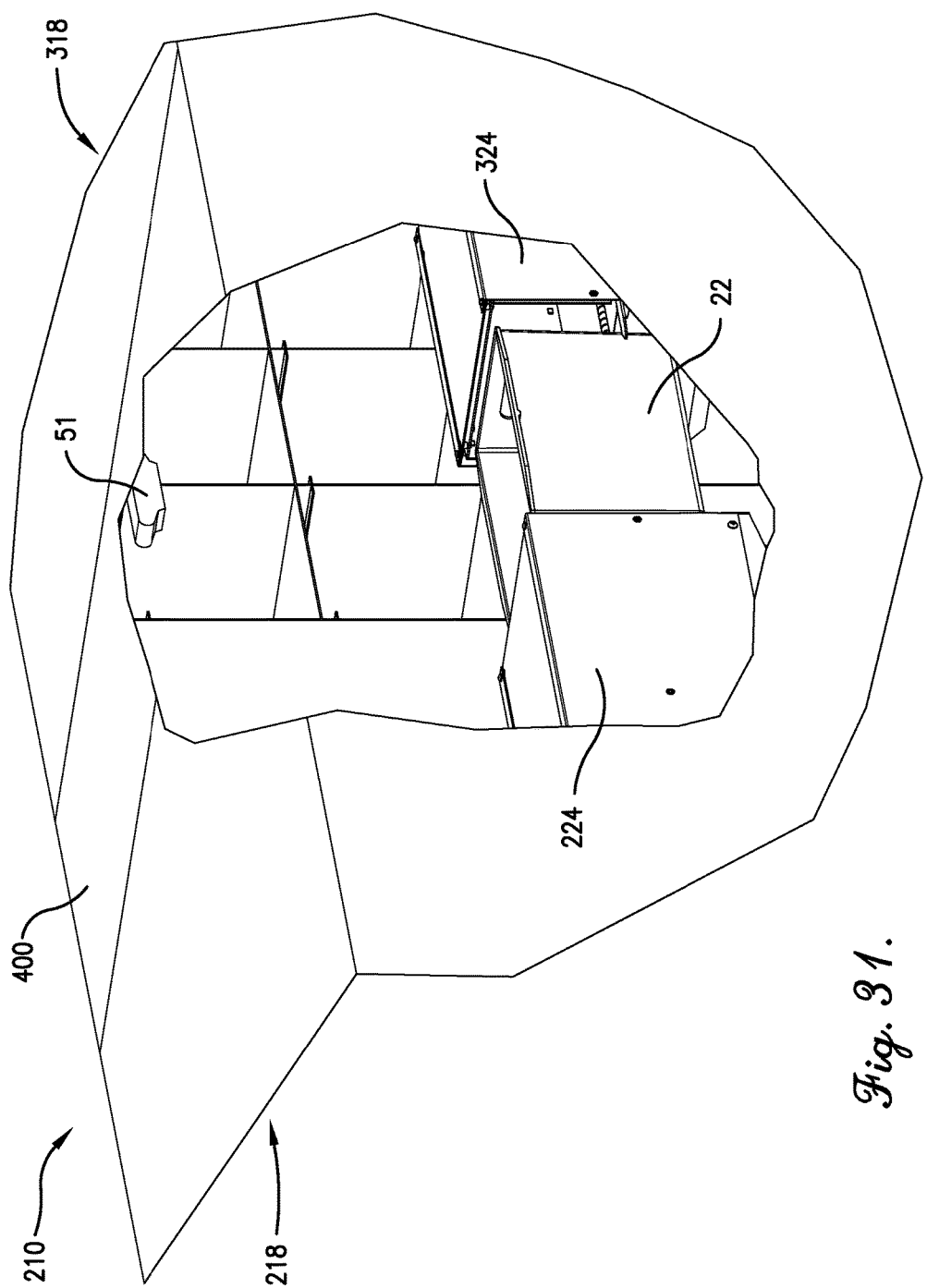
FIG. 31 is a fragmentary perspective view of the first storage matrix and a camera therein.

In some embodiments of the invention, as illustrated in FIGS. 4 and 5, a supplemental portion 92 of the outer housing 38 may be affixed to a front or to primary doors 44 of the storage matrix 18 and may cover the drawer scanners 26 affixed to the storage matrix 18, while still leaving a gap through which the drawer scanner 26 may read identification indicia 16 passing by the gap. The supplemental portion 92 may be configured to be removable from the primary doors 44, in cases where the drawer scanners 26 need servicing and/or replacement. In some embodiments of the invention, other electronics may also be held within the supplemental portion 92 of the outer housing 38. For example, one or more cameras 51 or other imaging devices may be placed somewhere within the outer housing 38, as illustrated in FIG. 31. In some alternative embodiments of the invention, the cameras 51 may be located within the supplemental portion 92 of the outer housing 38 along with the drawer scanner 26 and may be directed upward or downward toward the access openings 42, open access drawers 20, and/or the storage containers 22 therein. This may allow the prescription storage and retrieval system 10 to verify its contents via the control system 36 analyzing images captured by the camera 51 as the access drawer 20 is being opened or closed. The images obtained by the camera 51 may be saved via the control system 36 each time the access drawer 20 is closed and/or opened, supporting the requirement to verify the quantity of controlled substances on hand each time a controlled substance is accessed.

The cameras 51 may be stationary, fixed focal length cameras operating in areas with adequate lighting. A high degree of resolution may not be required, as long as the camera(s) 51 allows macroscopic identification of the items or prescriptions in the storage containers 22. The camera(s) 51 may be located anywhere within the prescription storage and retrieval system 10 for troubleshooting and/or for recording images of the storage containers' contents each time the storage containers 22 are moved by the transport system 24. The control system 36 may also retain images of the storage containers 22 and make them available for viewing in correlation with date/time stamps, user activities, and machine function. The camera(s) 51 may record pictures when there is human interaction with the prescription storage and retrieval system 10 such as when storage containers 22 are being moved into and out of the access drawers 20 and/or during a verification process after the primary doors 44 have been opened.

Furthermore, another one of the scanners, referred to herein as a transport scanner 28, may be mounted onto the trolley 86 and/or the attachment device 78 of the transport system 24, as illustrated in FIG. 11. The transport scanner 28 may be arranged and configured to scan the barcodes or other identification indicia 16 on the bags 14 and/or prescription batches 11 within the storage containers 22 as the storage containers 22 are picked up and/or dropped off by the transport system 24. In some embodiments of the invention, the transport system 24 further include a mirror 96, and the transport scanner 28 may be mounted so that it looks into the mirror 96 to see or scan the barcodes or identification indicia 16 on the bags 14 or prescription batches 11 in the storage container 22. Having the transport scanner 28 directed at the mirror 96 allows the transport scanner 28 to be at a correct focal distance from the barcodes or identification indicia 16 without adding substantially to an overall height of the trolley 86 and/or attachment device 78. Additionally, one or more of the cameras 51 described above may be positioned on the transport system 24 and may be configured to take a picture of the storage container's contents as the storage container 22 is moved into and/or out of the compartments 40 and/or the access drawers 20. In some embodiments of the invention, the cameras 51 on the transport system 24 may be mounted at any convenient, unobstructed location on or fixed relative to the trolley 86.

The sensors 30 are provided for detecting various compartment content status information, and may include optical or laser-based sensors, weight-based sensors, mechanically-activated sensors, or any other sensors known in the art for sensing a condition and providing a corresponding signal to the control system 36 indicating that condition. As illustrated in FIGS. 9-14, 18, and 20-23, at least some of the sensors 30 may be located in or around the access openings 42, the access drawers 20, and/or the compartments 40 of the storage matrix 18 and may be configured for detecting compartment content status information. For example, some of the sensors 30 may be configured to detect the presence of one of the storage containers 22, detect whether the storage container 22 is empty, and/or detect whether or not contents of the storage container 22 protrude outward of the storage container 22 (or protrude above a selected limit), also referred to herein as "overfill." These sensors 30 may report this information to the control system 36.

In some embodiments of the invention, one or more of the sensors 30 may also be placed on components of the transport system 24, such that information regarding ones of the storage containers 22 being held by and/or transported by the transport system 24 may also be communicated to the control system 36 via those sensors 30. These sensors 30 may be configured to sense whether one of the storage containers 22 is on, in, or attached to the transport system's trolley 86 or attachment device 78, whether that storage container 22 is empty, and whether the contents of that storage container 22 are protruding out of that storage container 22.

Figure 18:
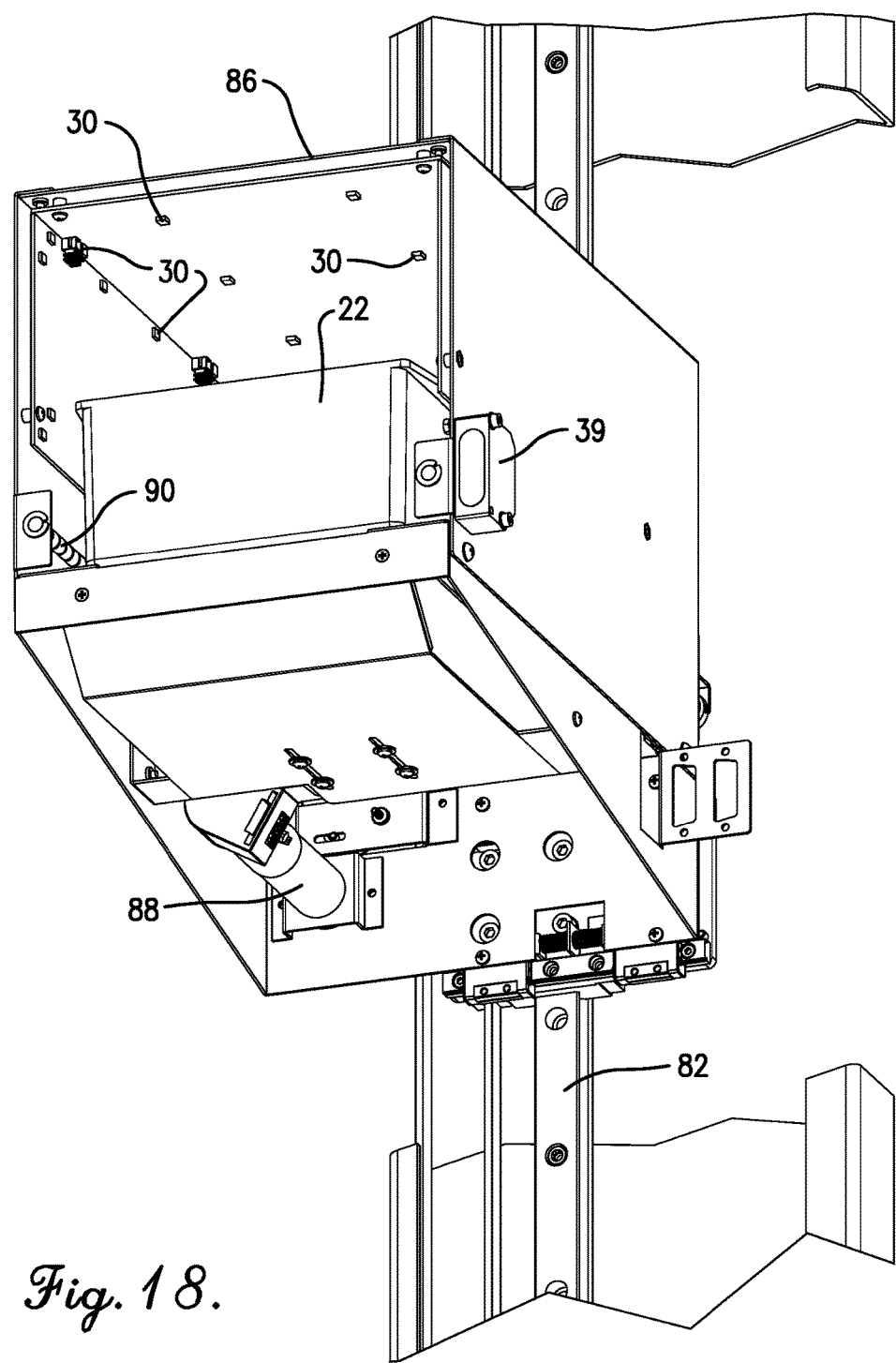
FIG. 18 is a fragmentary bottom front perspective view of the transport system, illustrating the storage container riding therein and the trolley traveling on the vertical tracks of FIG. 15.
Figure 19:
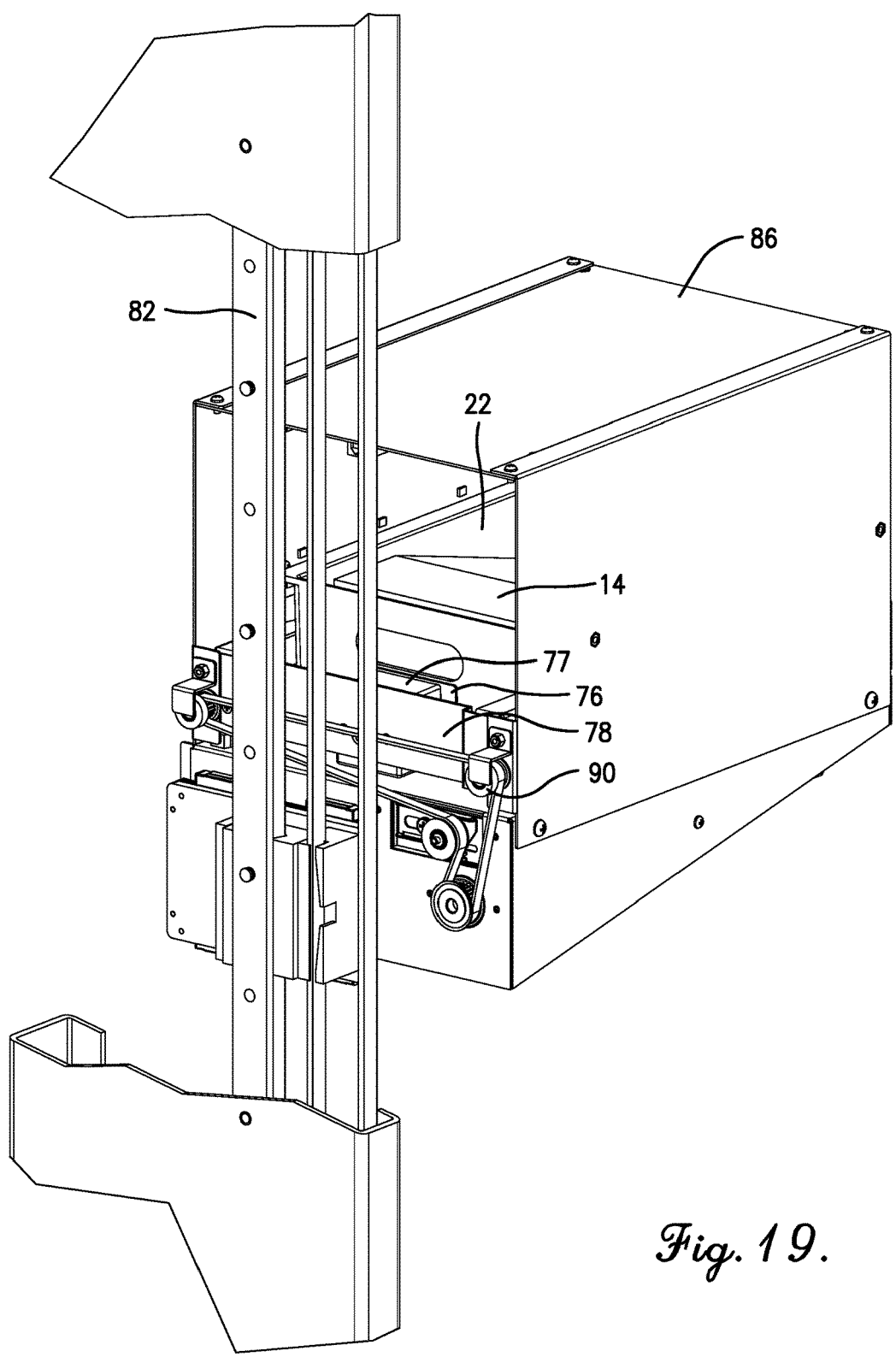
FIG. 19 is a fragmentary rear perspective view of the transport system of FIG. 18.
Figure 20:
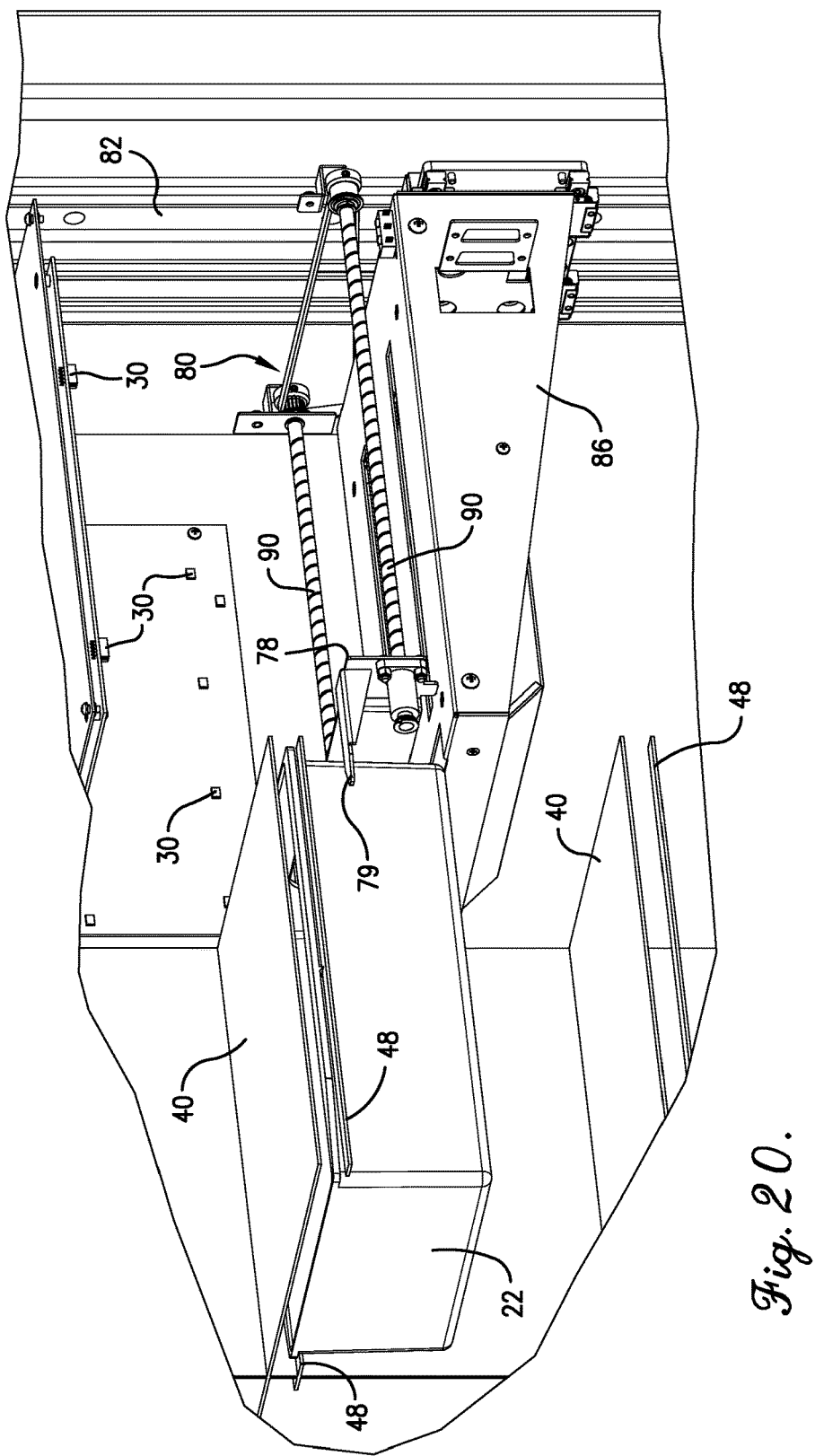
FIG. 20 is a fragmentary front and side perspective view of the transport system and one of the compartments of FIG. 2 with portions of the compartment removed, illustrating the transport system in the extended configuration placing the storage container into the compartment.
Figure 21:
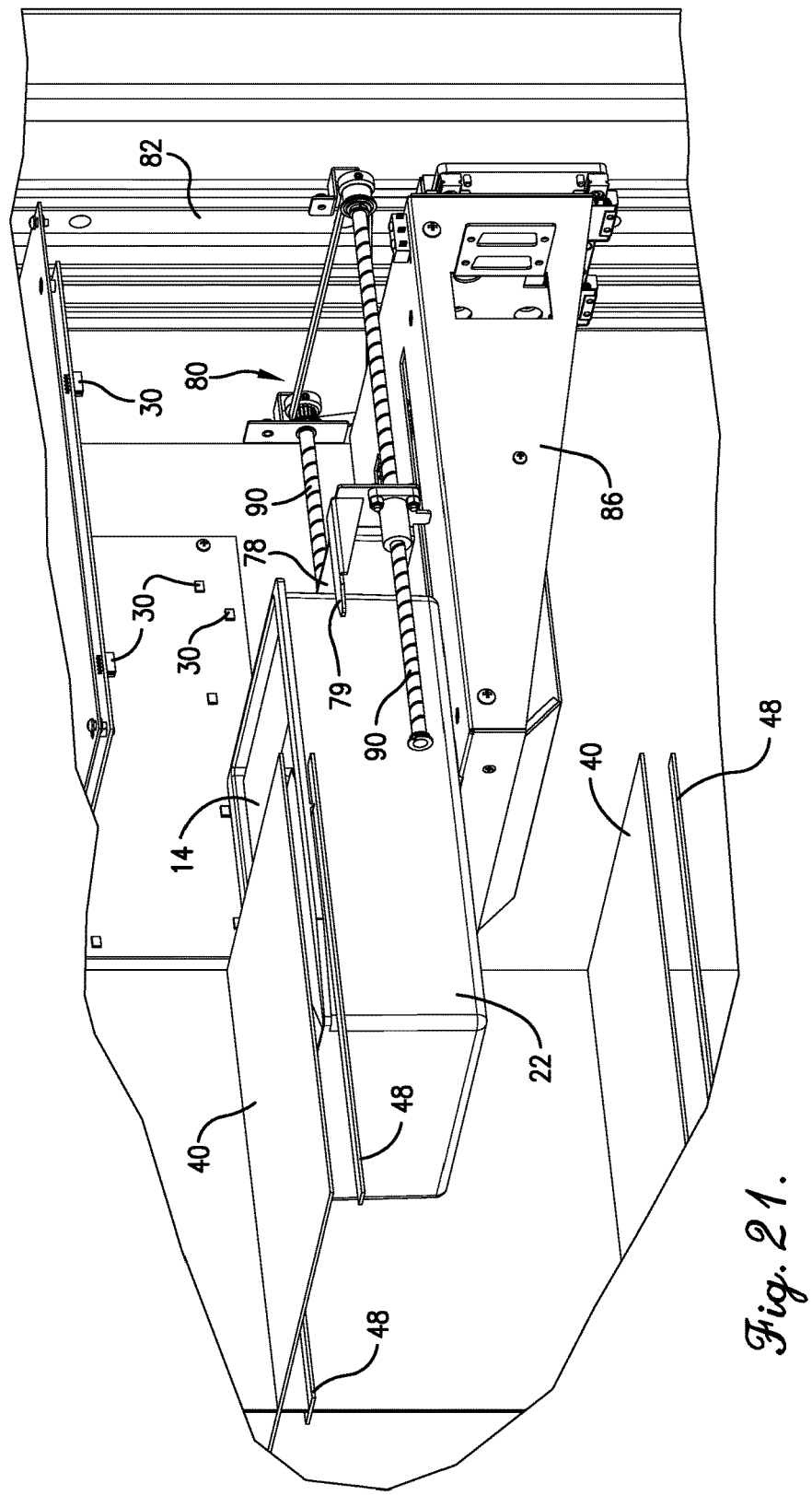
FIG. 21 is a fragmentary front and side perspective view of the transport system and the storage matrix compartment of FIG. 20, illustrating the transport system at a configuration part-way between the extended configuration and the retracted configuration, removing the storage container from the compartment.
Figure 22:
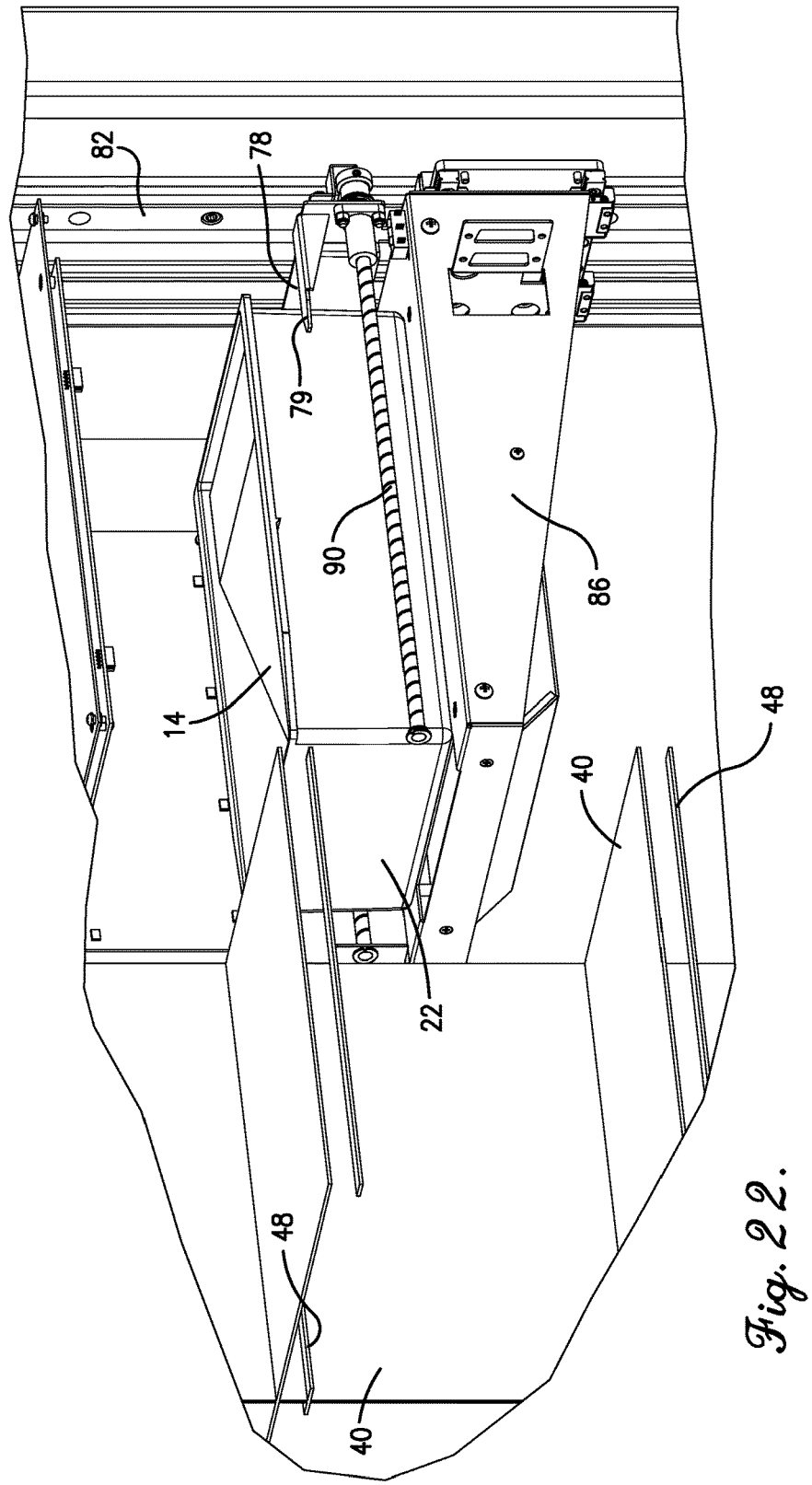
FIG. 22 is a fragmentary front and side perspective view of the transport system and the storage matrix compartment of FIG. 21, illustrating the transport system in the retracted configuration following removal of the storage container from the compartment.
Figure 23:
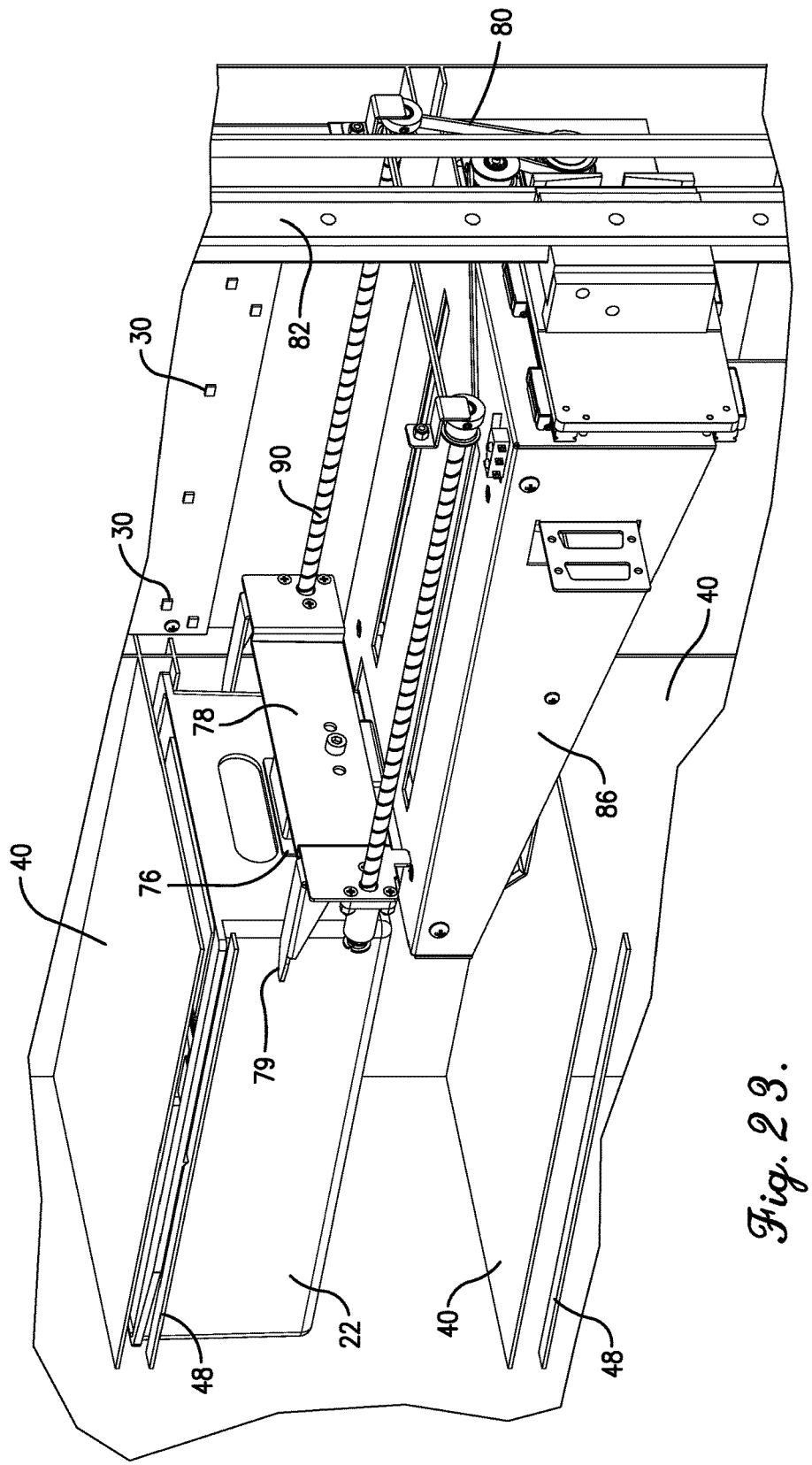
FIG. 23 is a fragmentary rear and side perspective view of the transport system and the storage matrix compartment of FIG. 20.
Figure 24:
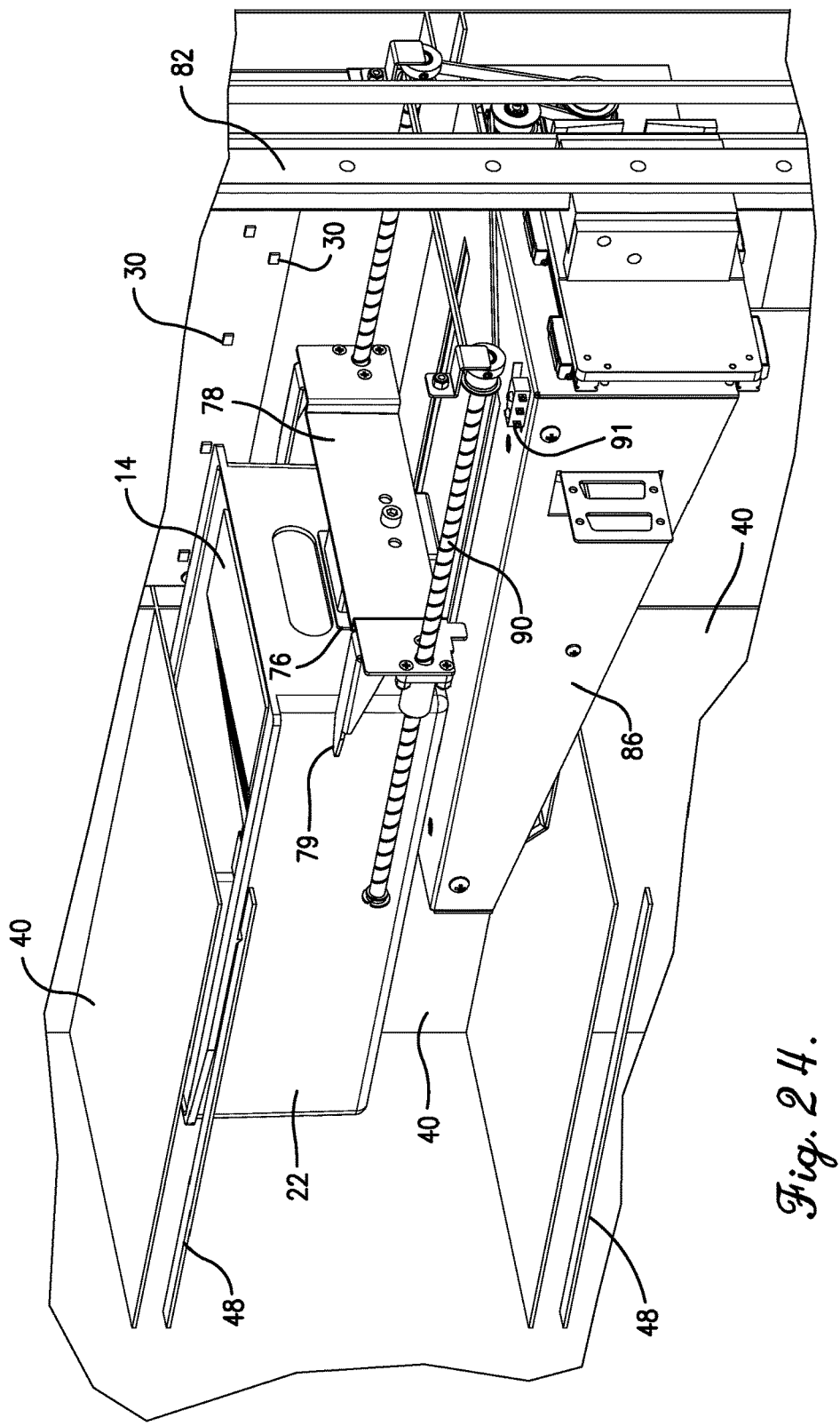
FIG. 24 is a fragmentary rear and side perspective view of the transport system and the storage matrix compartment of FIG. 21.
Figure 25:
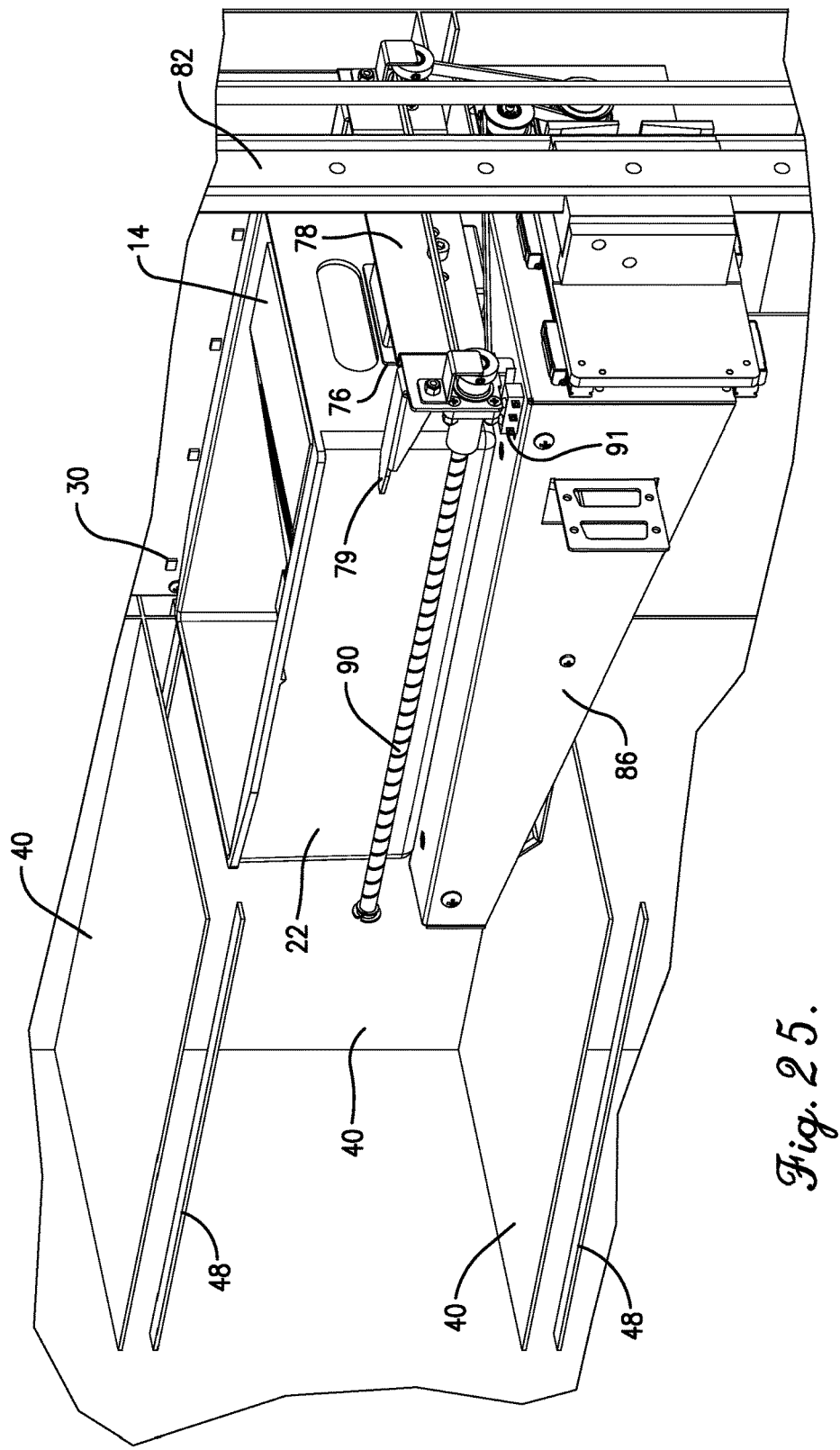
FIG. 25 is a fragmentary rear and side perspective view of the transport system and the storage matrix compartment of FIG. 22.

As illustrated in FIG. 18, the sensors 30 may also include one or more laser mapping sensors 39 mounted on or associated with the transport system 24 and/or the trolley 86 or attachment device 78 thereof. The laser mapping sensors 39 may be configured for aligning the trolley 86 with the compartments 40 of the storage matrix 18 and/or the access drawers 20. For example, the laser mapping sensors 39 may include lasers on the trolley 86 and light sensors on the compartments 40 or vice versa. Other laser mapping sensors may be used without departing from the scope of the invention.

Figure 8:
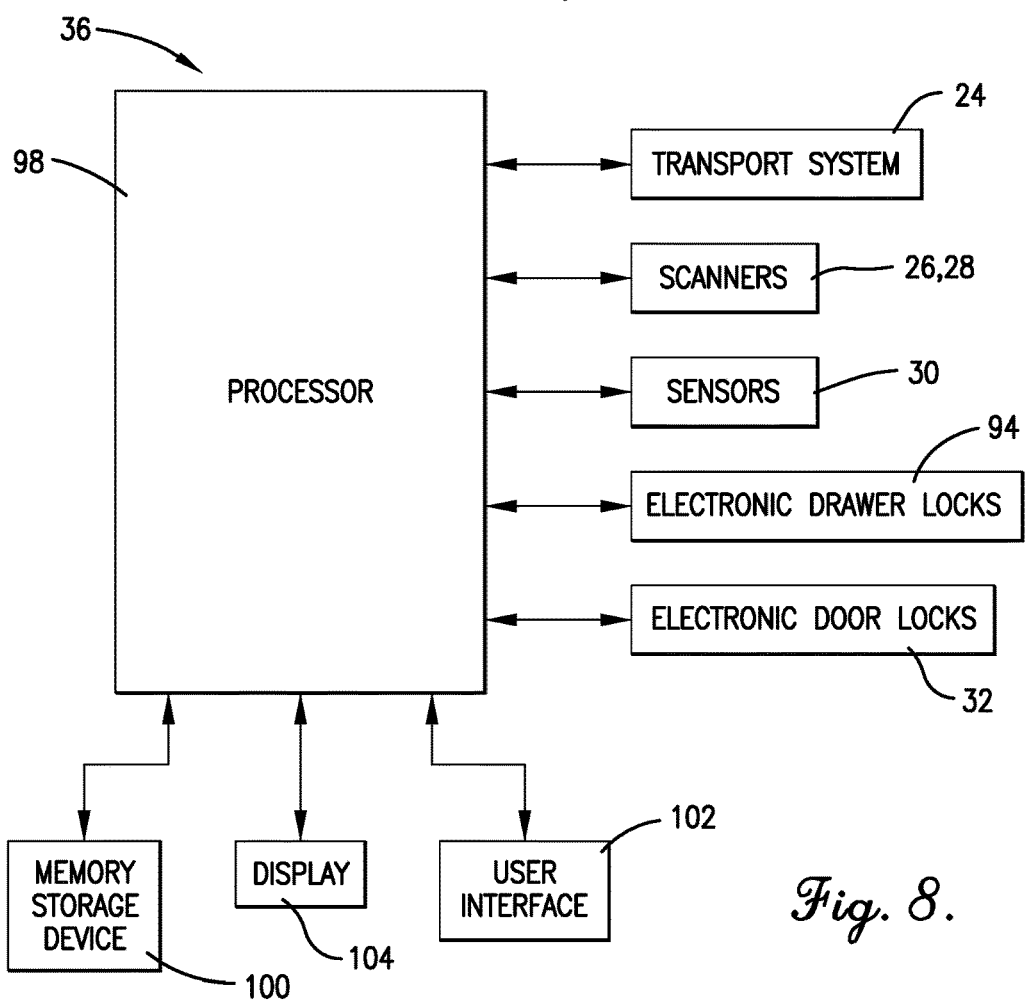
FIG. 8 is a schematic diagram of a control system of the prescription storage and retrieval system of FIG. 1.

The control system 36 may track prescriptions in the storage matrix 18 and control various operations of the prescription storage and retrieval system 10. As schematically illustrated in FIG. 8, the control system 36 may include a processor 98, associated memory storage devices 100, a user interface 102, and/or a display 104. The processor 98 may be communicably coupled with the transport system 24, scanners 26,28, sensors 30, electronic drawer locks 94, and electronic door locks 32, as well as the battery powered lock monitoring system 31. The control system 36 may generally be configured for authenticating that an individual is authorized to retrieve a particular prescription 12, tracking a location of any of the prescription batches 11 stored in the storage matrix 18, controlling the transport system's movements within the storage matrix 18, controlling activation and deactivation of the transport system's attachment device 78 to attach to and release any one of the storage containers 22, controlling the electronic door locks 32 or the electronic drawer locks 94 associated with the access drawers 20 at the access openings 42, and receiving and interpreting signals from any of the scanners 26,28 and sensors 30.

The processor 98 may include any computer or processor known in the art and may further include any number and combination of controllers, circuits, integrated circuits, programmable logic devices such as programmable logic controllers (PLC) or motion programmable logic controllers (MPLC), microcontrollers, other electrical and computing devices, and/or other data and signal processing devices for carrying out the functions described herein, and may additionally comprise one or more memory storage devices 100, transmitters, receivers, and/or communication busses and ports. The processor 98 may be configured for communication with actuators 80 of the transport system 24 for actuating components thereof to desired locations within the storage matrix 18 and may also receive feedback signals from the various sensors 30, scanners 26,28, and electronic door locks 32 described herein, as well as from other components described above. The processor 98 may communicate with and/or send command signals to various components of the prescription storage and retrieval system 10 and/or other pharmacy systems and pharmacy applications via wires, cables, and the like or via wireless means, such as Wi-Fi or the like. In some embodiments of the invention, the processor 98 may comprise several separate processors or computing devices which may communicate and exchange information with each other and may even be located in remote locations relative to each other. Furthermore, the processor 98 and/or the several processors or computing devices may each be configured to execute different steps, algorithms, subroutines, or codes described herein.

The processor 98 may be configured to implement any combination of the algorithms, subroutines, or code corresponding to method steps and functions described herein. The processor 98 and computer programs described herein are merely examples of computer equipment and programs that may be used to implement the present invention and may be replaced with or supplemented with other computers, processors, and/or computer programs without departing from the scope of the present invention. While certain features are described as residing in the processor 98 or control systems associated therewith, the invention is not so limited, and those features may be implemented elsewhere. For example, the associated memory storage devices 100 accessed by the control system 36 or its processor 98 may be located remotely from the processor 98 or control system 36 without departing from the scope of the invention.

In various embodiments of the invention, the processor 98 may implement a computer program and/or code segments to perform some of the functions described herein. The computer program may comprise an ordered listing of executable instructions for implementing logical functions in the processor. For example, the computer program may be a software program configured to run on a computer, such as a personal computer, laptop, tablet, or the like. The computer program can be embodied in any computer-readable medium for use by or in connection with an instruction execution system, apparatus, or device, and execute the instructions. In the context of this application, a "computer-readable medium" can be any physical means that can contain, store, communicate, propagate, or transport the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), a portable compact disk read-only memory (CDROM), an optical fiber, multi-media card (MMC), reduced-size multi-media card (RS MMC), secure digital (SD) cards such as microSD or miniSD, and a subscriber identity module (SIM) card.

As noted above, the control system 36 may comprise memory storage devices 100 or other various memory elements. The memory storage devices 100 may be integral with the control system 36, stand-alone memory, or a combination of both. The memory storage devices 100 may include, for example, removable and non-removable memory elements such as RAM, ROM, flash, magnetic, optical, USB memory devices, MMC cards, RS MMC cards, SD cards such as microSD or miniSD, SIM cards, and/or other memory elements. Specifically, the memory storage devices 100 may store at least a portion of the computer program or code segments described above, as well as user-specified preferences, information regarding user selections, prescription information, patient information, position or location information of various items within the storage matrix 18, user authentication information, scanner and/or sensor readings, location calibration information for the transport system 24, lock or primary door access logs, and the like.

The user interface 102 may be configured to receive information from a user, scanner, sensor, or the like and may be communicably coupled with the processor 98, the memory storage devices 100, the display 104, and/or other components of the prescription storage and retrieval system 10. The user interface 102 may comprise a mouse, keyboard, touch screen, switches, buttons, or various data input ports whereby the user may input data directly into the control system 36 or otherwise exchange information with the control system or its associated components. The user interface 102 may also include scanners and/or sensors, such as those described above, for authentication purposes. For example, the user interface 102 may include a card reader, such as a CAC card reader, a barcode scanner, a QR code scanner, and/or any other sensor or scanner for identifying and authenticating user actions. As illustrated in FIG. 1, these user interface scanners may be mounted anywhere on the outer housing 38 of the storage matrix 18 and may be used by the control system 36 or processor thereof to provide access to one of the doors or access drawers 20 based on valid or authenticated identification being scanned thereby, such as a barcode, QR code, RFID tag, or smart card information of an authenticated user. Additionally or alternatively, the user interface scanners may include identification via biometric readings such as a thumb print or a retina scan. In some embodiments of the invention, the user interface 102 may also include an E-stop or emergency stop button 106, switch, or the like, configured to quickly stop and/or shut down any of the electrically-operated components described herein, such as components of the transport system 24. In some embodiments of the invention, the user interface 102 may also include a power switch 109 for turning on power to the prescription storage and retrieval system 10.

As illustrated in FIG. 1, the display 104 or display screen of the control system 36 may be configured for providing visual graphics, text instructions, and other information to a user or operator. The display 104 may be communicably coupled with the processor 98 and/or motion control hardware, as later described herein, and may include a plurality of displays. In some embodiments of the invention, the display 104 or displays may be touch screens serving as an integrated display and user interface 102 in one. For example, a user may touch a visual depiction of a button or may touch a provided menu item provided on the display 104 via the processor 98 and/or the memory storage devices 100, and this touch may activate a command by the processor 98 to retrieve a particular prescription 12 from a particular location within the storage matrix 18.

In some embodiments of the invention, the display 104 may include indicator lights (not shown) associated with one or more of the access openings 42 and/or access drawers 20. For example, there may be lights and/or displays, mounted on any portion of the outer housing 38, access drawers 20, or access doors, that are configured for indicating a status and/or displaying text and other information. In some embodiments of the invention, the indicator lights may include multiple colors of lights or individual lights capable of displaying multiple colors, depending on the type of indication to be made. These indicator lights or displays may indicate to users where their retrieved prescription batches 11 are available or where empty storage containers 22 are available for storing new prescription batches 11.

Note that portions of the control system 36 described herein may be implemented on or by existing computer systems or pharmacy hardware. In some embodiments of the invention, a pharmacy workflow system that identifies patients as they arrive to pick up their prescriptions 12 or prescription batches 11 may use certain protocols to trigger the transport system 24 to deliver the storage container(s) 22 containing the correct prescription batches 11 to one of the access drawers 20 or access openings. For example, pharmacy workflow system may include various computers running workflow software programs thereon and/or may include various other processors, memory storage devices, actuators, and the like for assisting in pharmacy workflow and tracking of patient and prescription information. In some embodiments of the invention, the control system 36 may be integrated with and/or communicate with the pharmacy workflow system for performing the following: confirm that a pharmacist or pharmacy staff has verified a prescription 12 or prescription batch 11 before placing the prescription batch 11 into the storage matrix 18, confirm that verified prescription batches 11 are promptly stored in the storage matrix 18 or dispensed directly to a waiting patient and alert pharmacy management if neither of these options occur, and determine when prescriptions 12 or prescription batches 11 should be removed from the storage matrix 18 and returned to stock. Furthermore, the control system 36 and pharmacy workflow system may be integrated with and/or communicably coupled with inventory management systems to ensure secure and accurate return to stock procedures are followed. However, some or all of these functions may be performed directly by the control system 36 described herein without departing from the scope of the invention.

In some embodiments of the invention, motion control of the transport system 24 may be provided by an embedded system or computer program running on ScriptPro's X3xK motion control hardware 108 manufactured by ScriptPro International, Inc. of Mission, Kans. The motion control hardware 108, as illustrated in FIGS. 2 and 15, may include any number and combination of controllers, circuits, integrated circuits, programmable logic devices such as programmable logic controllers (PLC) or motion programmable logic controllers (MPLC), microcontrollers, other electrical and computing devices, and/or other data and signal processing devices for carrying out the functions described herein, and may additionally comprise one or more memory storage devices 100, transmitters, receivers, and/or communication busses and ports. The motion control hardware 108 may be configured for communication with actuators 80 of the transport system 24 for actuating components thereof to desired locations within the storage matrix 18 and may also receive feedback signals from the various sensors 30, scanners 26,28, and electronic locks 32,94 described herein, as well as from other components described above. The motion control hardware 108 may communicate with and/or send command signals to various components of the prescription storage and retrieval system 10 via wires, cables, and the like or via wireless means, such as Wi-Fi or the like. The motion control hardware 108 may be configured to implement any combination of the algorithms, subroutines, or code corresponding to method steps and functions described herein. The motion control hardware 108 described herein are merely examples of equipment and programs that may be used to implement the present invention and may be replaced with or supplemented with other computers, processors, and/or computer programs without departing from the scope of the present invention. In various embodiments of the invention, the motion control hardware 108 may implement code segments to perform some of the functions described herein. The code segments can be embodied within the motion control hardware 108. The motion control hardware 108 may interface via a serial connection to a computer and/or the processor 98 of the control system 36 described herein. Furthermore, the sensors 30 may include embedded controls that interface to the processor 98 and/or the motion control hardware 108 via combination USB and serial connections.

In some embodiments of the invention, the prescription storage and retrieval system 10 may be extended to include patient-facing elements such as conveying means to deliver prescriptions to patients at walk up or drive-in locations, patient identification facilities, point of sale facilities, electronic signature facilities, and audio and/or video facilities for users to engage in remote communications with patients to assist them in retrieving their prescription batches 11 and counsel them regarding proper medication use. For example, one or more of the access drawers 20 may be replaced with and/or configured to operate in conjunction with supplemental transport systems, chutes, or the like which may deliver the prescription to a secondary location as needed, such as to drive-in pickup areas. Furthermore, the control system 36 may be configured to direct prescription batches 11 to these secondary locations based on a location of the user interface 102 used during authentication of the user. If the prescription batches 11 or items to be transferred to the secondary location are not successfully transferred to a remote device for transport thereto, the control system 36 may command a return of the storage container 22 with the prescription 12 still therein to the trolley 86 or a selected one of the compartments 40 and may provide an error message to the user via the display 104 or user interface 102.

Figure 30:
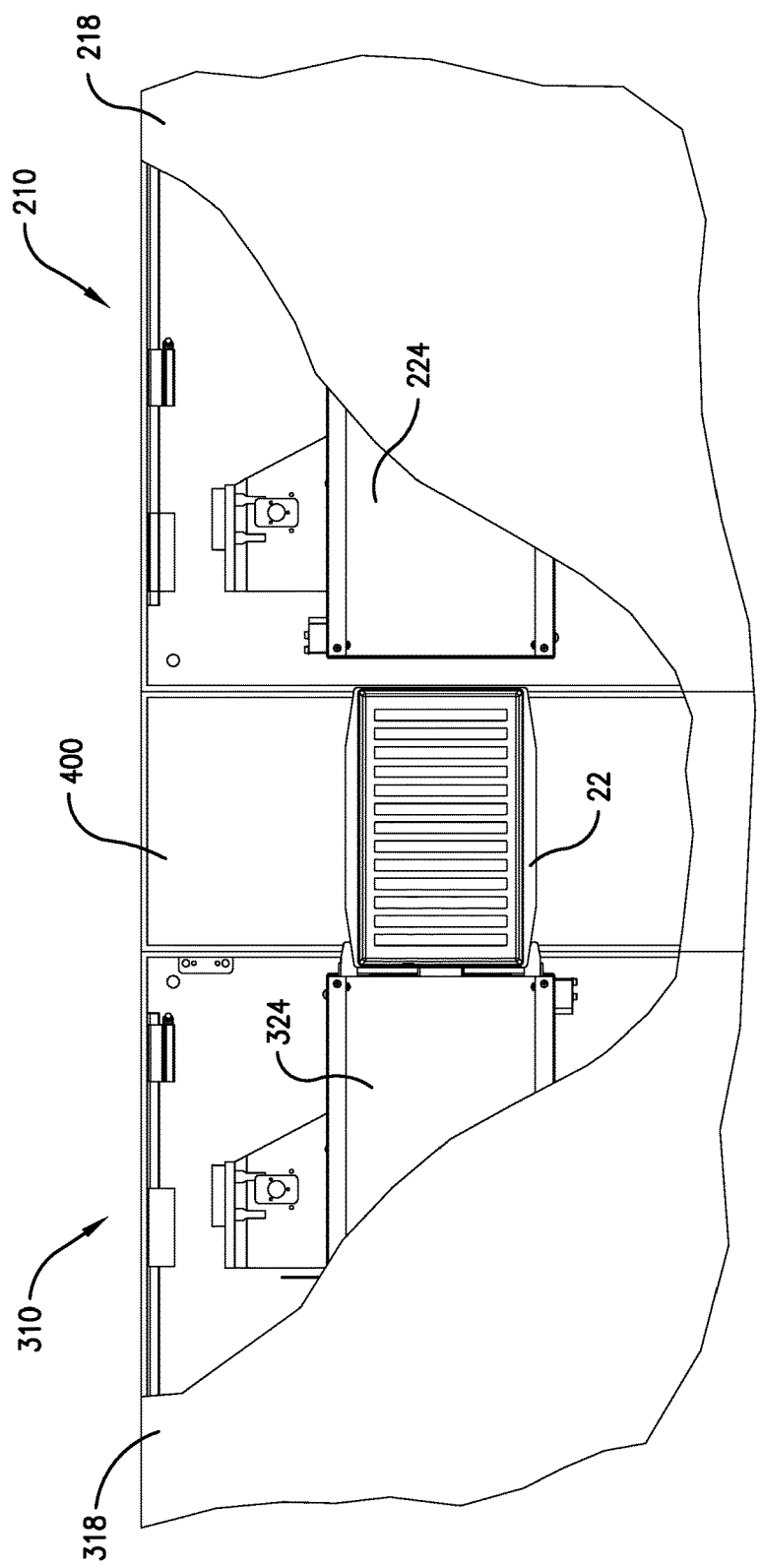
FIG. 30 is a top plan view of an alternative embodiment of the invention illustrating transfer of a storage container between a first storage matrix and a second storage matrix.

In some embodiments of the invention, the prescription storage and retrieval system 10 may be scalable and modular, such that multiple storage matrices may be connected together. For example, as illustrated in FIG. 30, two storage matrices, a first storage matrix 218 and a second storage matrix 318, may be attached together via a connecting unit 400. The multiple storage matrices 218,318 may be connected in various ways through multi-sided connecting units, such as linearly aligned (as in FIG. 30), back-to-back, perpendicular (right angle) with each other, and/or stacked with one storage matrix in front of another, having the ability to pull the front storage matrix to service the back storage matrix behind it. The connecting units may also allow the transport system trolley 86 or attachment device 78 to access all compartments 40 in the resulting integrated system.

In some embodiments of the invention, the first storage matrix 218 and the second storage matrix 318 may each be part of independent systems 210,310 substantially identical to prescription storage and retrieval system 10, having independent control systems which may communicate with each other, as well as a first transport system 224 and a second transport system 324, each substantially identical to the transport system 24. In some embodiments of the invention, both the first and the second transport systems 224,324 may be configured to rotate, such that when the transport systems 224,324 reach the connecting unit 400 positioned therebetween, they may be rotated to substantially face each other and/or the connecting unit 400. Rotation may be controlled in an automated fashion by communicably coupled control systems of each of the independent systems 210,310 or by a shared control system. Furthermore, as illustrated in FIG. 31, cameras in either of systems 210,310, substantially identical to the cameras 51 described above, may record video or images detailing contents of the storage containers 22 both before and after transfer of packages of storage containers (such as storage containers 22) between the first storage matrix 218 and the second storage matrix 318.

In some embodiments of the invention, a cabinet-only model of the second storage matrix 318, without the access drawers 20, may be connected with the first storage matrix 218 or the prescription storage and retrieval system 10, thus providing additional storage space at a lower cost. Other components of the prescription storage and retrieval system 10 may also be omitted from the add-on storage matrices, such as the displays 104, the control system 36 in general, and/or any scanners 26,28 or sensors 30 specifically associated with the access drawers 20, without departing from the scope of the invention.

Some embodiments of the invention may also include bulk storage areas (not shown). For example, a bulk storage area may replace a plurality of adjacent compartments 40 in the storage matrix 18 and may be configured for drug storage and reverse distribution storage. When used for drug storage, the control system 36 and/or some of the scanners 26,28 may track the drugs placed therein. Likewise, when used for bulk distribution, the control system 36 and/or some of the scanners 26,28 may track the drugs and returned prescriptions therein. The outer housing 38 may additionally include a bulk storage door (not shown) with an electronic door lock, similar to the electronic door lock 32 and/or the electronic drawer lock 94. In some embodiments of the invention, a separate security access authorization can be set for each bulk storage area as desired. The bulk storage area may house boxes or packages containing multiple medication bottles or multiple medical items. Barcodes or identification indicia 16 as described above may be placed on the individual items and/or on the boxes or packages therein. The identification indicia 16 on the boxes or packages may designate the medication bottles or sub items contained therein, including information such as lot numbers, expiration dates, inventory track and trace data, and number of drug units or items contained in each.

In some embodiments of the invention, the bulk storage areas and the bulk storage door may cooperatively form a drug storage vault that securely stores high-risk and/or high-cost medications. Additionally or alternatively, the prescription storage and retrieval system 10 may include separate bulk storage area(s) and drug storage vault(s). Access to the bulk storage area(s) and/or the drug storage vault(s) may be limited to only certain users via the control system 36 and/or physical locks and keys. However, any access-limiting locking configurations may be used with the bulk storage area(s) and/or the drug storage vault(s) without departing from the scope of the invention.

In operation, users may place the prescription batches 11 in an empty one of the storage containers 22 presented at one of the access openings 42 or in one of the access drawers 20. Using a secure process, the identity of the prescriptions 12 within the prescription batches 11 may be determined and transmitted to the control system 36 or the processor 98 thereof. The control system 36 may then instruct the transport system 24 to move that storage container 22 to an open location (i.e., an empty compartment 40) in the storage matrix 18 for secure storage. The control system 36 tracks and/or records location information regarding where the prescription 12 is stored within the storage matrix 18.

For retrieval of prescription 12 from the storage matrix 18, the control system 36 may require authentication of a user via the user interface 102. When an authenticated user accesses the control system 36 and/or its user interface 102 to request particular prescription batches 11, the control system 36 may command the transport system 24 to retrieve corresponding ones of the storage containers 22, based on location information stored in the memory storage device 100, and may command the transport system 24 to place the retrieved storage container 22 in an available one of the access drawers 20 associated with the access openings 42. The control system 36 may also command associated ones of the electronic drawer locks 94 to unlock, such that the user can then remove the prescription batch 11 from that access drawer 20. The user may also be notified which of the access drawers 20 to open via the display 104 or displays of the control system 36. The control system 36 may also record and/or store into the memory storage device 100 what individuals have access to any of the access doors, access drawers 20, or primary doors 44 of the storage matrix 18, as well as when such access has occurred by any of those authenticated individuals. This may allow pharmacy management to investigate suspected drug diversion.

Figure 26:
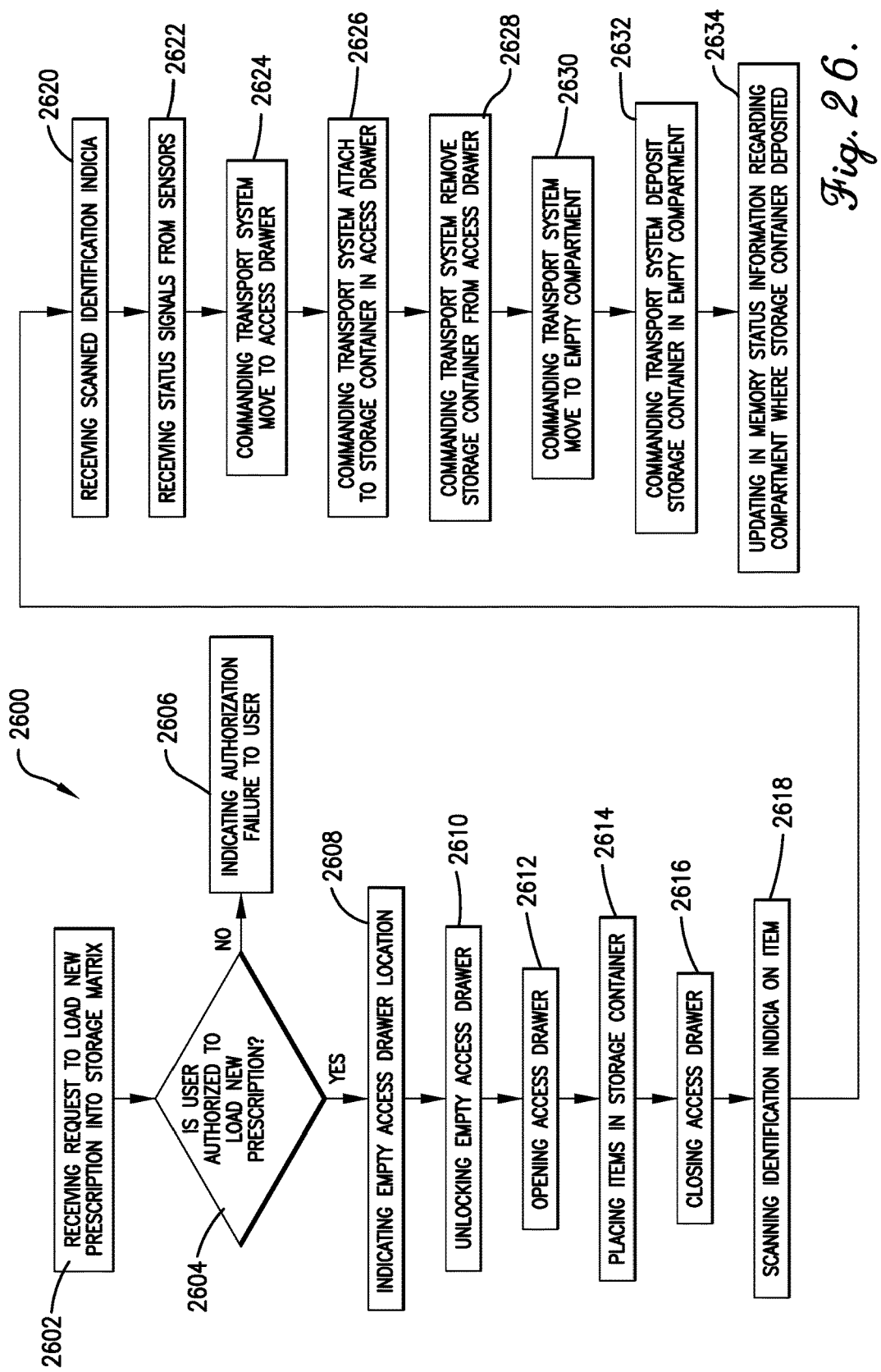
FIG. 26 is a flow chart describing a method of loading the prescription storage and retrieval system of FIG. 1 in accordance with an embodiment of the present invention.
Figure 27:
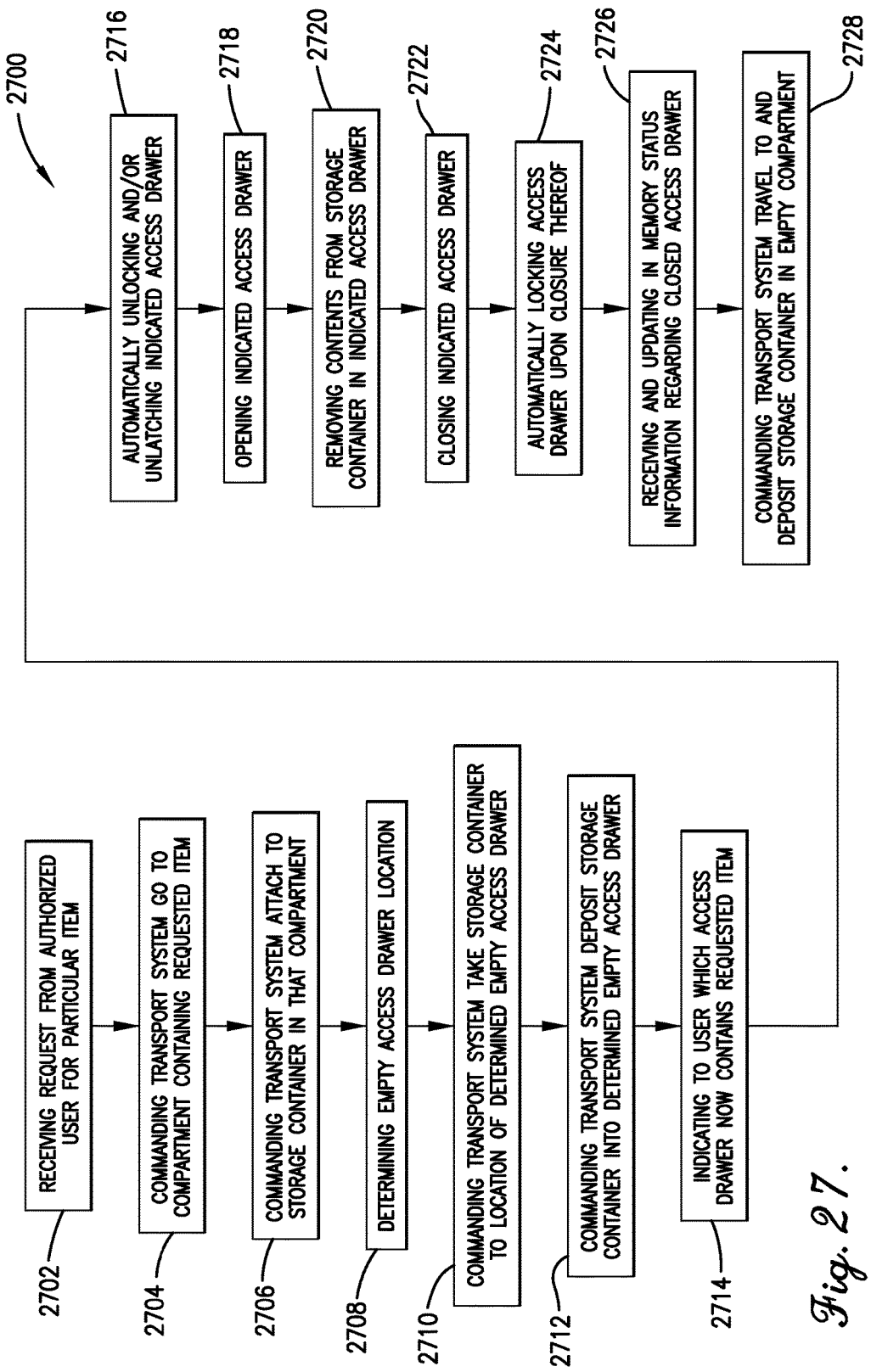
FIG. 27 is a flow chart describing a method of retrieval of a prescription from the prescription storage and retrieval system of FIG. 1 in accordance with an embodiment of the present invention.

Flow charts of a method 2600 for securely storing prescriptions and a method 2700 for authorized retrieval of prescriptions for patient pickup is illustrated in FIGS. 26 and 27. In this regard, some of the blocks of the flow charts may represent a module segment or portion of code of a program of the present invention which comprises one or more executable instructions for implementing the specified logical function or functions. In some alternative implementations, the functions noted in the various blocks may occur out of the order depicted. For example, two blocks shown in succession may in fact be executed substantially concurrently, or the blocks may sometimes be executed in reverse order depending upon the functionality involved.

Loading

The method 2600 for securely storing prescription batches for patient pickup may include the steps of receiving a request to load a new prescription into the storage matrix 18, as depicted in block 2602, and authenticating the user making this request, as depicted in block 2604. These steps may be performed by the control system 36 receiving user-entered or user-provided identification information about the prescription 12 and/or about the user. Information about the prescription 12 may include any patient and/or prescription information typically entered in a pharmacy workflow system, such as name, address, contact information, age, sex, doctor, relevant dates, dosing information, prescription name, number of refills, and the like. Proof of identity or other similar inputs used to authorize a user for loading prescriptions into the storage matrix 18 may include scanner data received from a barcode on an identification card belonging to the individual or a particular password typed in or otherwise entered via the user interface 102. For example, a pharmacy staff member may insert a smartcard into a reader on a front of the storage matrix 18 and/or may scan a barcode on an ID badge. Additionally or alternatively, other biometric information may be required during this authentication step, such as a finger or thumb print, a retinal scan, or the like.

To perform the authenticating step 2604, the control system 36 may also determine if the user is authorized by matching authorized user data stored in the memory storage device 100 with the identity information entered or otherwise provided by the user. If an authorized match is not found, the method 2600 may include a step of indicating authorization failure on the display 104 or via the user interface 102 audibly and/or visually, as depicted in block 2606. However, if an authorized match is found and the user is thus identified to be an authorized user, and the method 2600 may then include a step of indicating on the display

104 an empty access drawer location having an empty storage container 22 therein, as depicted in block 2608, and unlocking this access drawer 20 or associated access door, as depicted in block 2610. Unlocking of the access drawer 20 may include the control system 36 sending an unlock command signal to one of the electronic drawer locks 94 associated with that one of the access drawers 20. This may result in the electronic drawer locks 94 being withdrawn from the access drawer 20 and/or being moved out of a pathway of travel of the access drawer 20. Note that if there is no empty access drawer 20 with an empty storage container 22 therein, the control system 36 may instruct the transport system 24 to retrieve one, using any of the retrieval methods later described herein.

Once the access door or access drawer 20 is unlocked, the method 2600 may include a step of the authorized user opening the access drawer 20 or door, as depicted in block 2612, sliding the storage container 22 therein at least partially outward through the associated access opening 42 as illustrated in FIGS. 4 and 5. Then the method 2600 may include a step of placing the prescription batch 11 therein, as depicted in block 2614. The bag 14 or prescription batch 11 may be placed in a preferred orientation such that the barcode or identification indicia 16 faces the drawer scanner 26. For example, in some embodiments of the invention, the bag 14 or prescription batch 11 may be placed with a barcode face down such that the drawer scanner 26 pointing upward below the access drawer 20 may read the barcode through the plurality of slots 70 or openings formed through the bottom wall of the storage container 22 as the access drawer 20 is closed. However, other scanning arrangements may be used without departing from the scope of the invention. Directions may be provided or displayed to the user via the control system 36 and the display 104 regarding how to load and properly orient the bag 14 or prescription batch 11 in the storage container 22 and/or access drawer 20.

Next, the method 2600 may include a step of the user pushing the access drawer 20 closed, as depicted in block 2616. Alternatively, this step may be replaced with the user sliding the storage container 22 back through the access opening 42 and closing the access door. However, other methods of closing off the access opening 42 after loading of the prescription batch 11 into the storage matrix 18 may be used without departing from the scope of the invention. Closing the access drawer 20 may also include automatic locking of the electronic drawer locks 94 or other locking devices associated with the access drawer to prevent unauthorized opening thereof.

The method 2600 may also include a step of scanning, with the associated scanner 26, the barcode or identification indicia 16 displayed on the bag 14 or packaging holding the prescription batch 11, as depicted in block 2618. This step may be performed as the storage container 22 passes through the access opening 42, causing the barcode or identification indicia 16 to pass by the drawer scanner 26. In some alternative embodiments of the invention, the user may manually scan each prescription item using a wired, wireless, or handheld indicia scanner (not shown) prior to placing the prescription batch 11 into the access drawer 20 or the storage container 22.

The method 2600 then may include a step of transmitting the scanned barcode or identification indicia 16 (or data representative thereof) back to the control system 36, as depicted in block 2620. This allows the control system 36 to determine identification information about the prescription 12 and/or the patient associated therewith and also allows the control system 36 to determine to which one of the access drawers 20 the transport system 24 should go to pick up the storage container 22 holding that prescription 12. As noted above, locations or coordinates of access drawers 20 associated with any of the drawer scanners 26 described herein may be stored in memory, such that when a barcode or identification indicia 16 is received from that drawer scanner 26, that identification information is automatically associated in the memory storage device 100 with the corresponding location or coordinates associated with that drawer scanner 26.

Once the prescription batch 11 is loaded and the access drawer 20 or access door is closed, the method 2600 may include step of the control system 36 receiving package status signals from sensors 30 of the access drawer 20 and/or access opening 42, as depicted in block 2622. Specifically, the sensors 30 associated with the access drawer 20 or access opening 42 through which the prescription batch 11 was loaded may send updated package status signals to the control system 36 or the processor 98 thereof indicating that a storage container 22 is in the access drawer 20 or compartment 40 thereof, indicating that the storage container 22 therein is not empty, and/or indicating that the storage container 22 therein is or is not overfull or sticking upward or outward therefrom. Each time one of the storage containers 22 are moved by the transport system 24 for storage and/or prescription retrieval, the contents of the storage container 22 may be verified by the sensors 30 in the transport system 24 or trolley 86 and/or in the access drawer 20.

Note that if the updated package status signals indicate to the control system 36 that there is no storage container 22 in the access drawer 20 when it is closed, the control system 36 may determine if an empty storage container 22 should be moved to the access drawer 20 so that it is ready to accept an item to be stored, or if the access drawer 20 should be left empty so it is ready to receive another storage container 22 with an item for retrieval. If one of the storage containers 22 is to be moved to the access drawer 20, the control system 36 may be configured to determine whether a large-sized storage container 64 or one of the small-sized storage containers 66 should be moved thereto. These determinations may be based on configuration settings and performance metric calculations within the control system 36. The control system 36 may also allow a user to request that one of the storage containers 22 of a specified size be moved to one of the access drawers 20.

Next, the method 2600 may include the steps of commanding the transport system 24 to move to the access drawer 20 or access opening 42 at which the prescription 12 and its associated storage container 22 are located, as depicted in block 2624, commanding the transport system 24 to attach the attachment device 78 thereof to the storage container 22, as depicted in block 2626, and commanding the transport system 24 to remove the storage container 22 from that access drawer 20, as depicted in block 2628. For example, to get one of the storage containers 22 from one of the access drawers 20 or compartments 40, the electromagnet 77 of the attachment device 78 may be extended via the drive screws 90 and powered on to magnetically engage with or attach to the metal plate or attachment portion 76 of the storage container 22, as illustrated in FIGS. 10 and 13. Then the storage container 22 may be pulled onto the trolley 86 via actuation of the drive screws 90 in a reverse direction, as illustrated in FIGS. 9 and 12.

Then the method 2600 may include the steps of commanding the transport system 24 to move to an empty compartment 40 of the storage matrix 18, as depicted in block 2630, and commanding the transport system 24 to deposit the storage container 22 into that empty compartment 40 of the storage matrix 18, as depicted in block 2632. Specifically, the control system 36 or its processor 98 may retrieve information from the memory storage device 100 and/or from various sensors 30 to determine a location of an empty one of the compartments 40 within the storage matrix 18. The control system 36 may command the trolley 86 thereof to then move vertically and/or horizontally to the coordinates of an empty one of the compartments 40, via actuation of the trolley 86 on the tracks 82,84 and/or actuation of one or more of the tracks 82,84 relative to each other, and then dispense the storage container 22 into that empty one of the compartments 40. In some embodiments of the invention, to release one of the storage containers 22 from the transport system 24 to one of the compartments 40, the electromagnet 77 of the attachment device 78 may again be extended via the drive screws 90 to push the storage container 22 into the compartment 40 or access drawer 20, and the electromagnet 77 may be powered down to release the storage container 22.

The method 2600 may further include a step of receiving and updating status information regarding that compartment 40 in the memory storage device 100 or other databases accessible by the control system 36 or its processor 98, as depicted in block 2634. For example, the control system 36 may receive signals from the transport scanner 28 or sensors 30 of the transport system 24 indicating identification indicia 16 of the bag 14 or prescription batch 11 being transported thereby, indicating if the storage container 22 being transported thereby is empty, indicating if the prescription batch 11 is too large or protruding above a top of the storage container 22 being transported thereby, etc. The control system 36 may also receive feedback from the transport system 24 indicating that the storage container 22 was dropped off or released at a particular location, which location may then be stored or associated with corresponding prescription identification information in the memory storage device 100, for later retrieval. As noted above, the memory storage device 100 may include remotely accessible memory and/or cloud storage memory without departing from the scope of the invention.

In some embodiments of the invention, errors may occur during loading of the prescription 12. Thus, to resolve errors detected by the sensors 30 or scanners 26,28, the following corrective actions may be performed. First, the control system 36 may indicate via the display 104 or user interface 102 an access drawer or compartment location experiencing an error. This may be, for example, an audible beep, a flashing light on or in close proximity to the access drawer 20 in which the error has occurred, or a display screen may provide text, a location number, or a graphic which assists the user in locating the access drawer 20 associated with the error. The error may be, for example, an overload condition, with a sensor indicating that the bag 14 or prescription batch 11 is extending too far outward of the storage container 22. Additionally or alternatively, the error may be a sensor indicating that an item was placed into the access drawer 20 but the drawer scanner 26 was not able to scan its barcode or identification indicia 16. For example, the item placed therein may either have been placed incorrect, may be missing the required identification indicia 16, and/or may be an item that does not belong in the storage matrix 18. Alternatively, the associated drawer scanner 26 may be broken or communication between the drawer scanner 26 and the control system 36 may have malfunctioned in some other way.

In response to this error signal, the user and/or pharmacy staff may repeat the authentication steps described above to obtain access to (i.e., unlock and open) the access drawer 20 associated with the error. The user may then remove the items therein, reposition or replace the items therein, and/or initiate a manual load via the user interface 102. For example, the user may manually type in the barcode and/or use an external scanner outward of the storage matrix 18 in order to scan in the prescription batch 11. Finally, once the access drawer 20 is closed and locked again, the sensors 30 may communicate with the control system 36 such that the control system 36 verifies that the storage container 22 is empty if an item was not scanned or verifies that the storage container 22 is not empty if an item was scanned during these corrective steps.

The method 2600 steps may be repeated to load any plurality of prescriptions into the storage matrix 18. In some embodiments of the invention, the method 2600 may include continued monitoring, such that the control system 36 may indicate via the display 104 or communication with other electronic devices when a prescription has been in the storage matrix 18 for longer than a threshold amount of time (e.g., the prescription 12 is past its maximum pick-up date or is expired). Furthermore, the control system 36 may display information regarding the stored items, including metadata from external applications, on the display 104 to be viewed by the user to help locate items in the prescription storage and retrieval system 10 as needed.

Retrieval

As illustrated in FIG. 27, the method 2700 for authorized retrieval of prescriptions for patient pickup may include a step of receiving a request from an authorized user for a particular prescription, as depicted in block 2702, which may include similar or identical authorization steps as those in steps —2602-2606 in the method 2600 described above and illustrated in FIG. 26. For example, the user may enter proof of identity, along with their requested prescription information, which may then be matched by the control system 36 or its processor 98 with authenticated users and corresponding prescriptions stored in the memory storage device 100. The request for the prescription 12 may be made via the user interface 102 and/or from the pharmacy's workflow system integrated with and/or communicably coupled with the control system 36 described herein. Additionally or alternative, a prescription code on a receipt, smart phone screen, or the like may be scanned and the control system 36 may identify a particular patient and/or prescription with which the prescription code is associated.

The method 2700 may then include a step of the control system 36 commanding portions of the transport system to travel to the compartment 40 containing the requested prescription 12, bag 14, prescription batch 11, or item, as depicted in block 2704, and commanding the attachment device 78 to attach to the storage container 22 in that compartment 40, as depicted in block 2706 and illustrated in FIGS. 20-25. Specifically, the trolley 86 and/or attachment device 78 may be actuated to the coordinates associated in the control system's memory storage device 100 with the requested prescription, then the electromagnet 77 of the attachment device 78 may be extended via actuation of the drive screws 90 and subsequently or simultaneously powered on, thus magnetically engaging with or attaching to the metal plate or attachment portion 76 of the storage container 22 holding the requested prescription 12. Then the storage container 22 may be pulled onto the trolley 86 via actuation of the drive screws 90 in a reverse direction. Note that the memory storage device 100 may be automatically updated, via one of the sensors 30 described above, as a result of step 2706 and/or as a result of any step herein where one of the storage containers 22 is removed from one of the compartments 40. For example, the compartment content status for an associated one of the compartments 40 may be changed or updated from "occupied" to "empty" once the storage container 22 is removed from the compartment 40 in step 2706.

Next, the method 2700 may include the steps of the control system 36 determining which access drawer 20 or associated compartment 40 is empty based on sensor readings and/or information retrieved from the memory storage device 100, as depicted in block 2708, and commanding the transport system 24 to move the storage container 22 attached thereto to a location or coordinates of the empty access drawer 20 or associated compartment 40, as depicted in block 2710. Once at the empty access drawer 20 or compartment 40, the method 2700 may include a step of commanding the transport system 24 to deposit the storage container 22 into that empty access drawer 20 or empty compartment 40, as depicted in block 2712. Specifically, as previously described herein, to release one of the storage containers 22 from the transport system 24 to the empty access drawer 20 or compartment 40, the electromagnet 77 of the attachment device 78 may again be extended via the drive screws 90 to push the storage container 22 into the compartment 40 or access drawer 20, as illustrated in FIGS. 9-10, and the electromagnet 77 may be powered down to release the storage container 22.

Once the requested prescription 12 is in the access drawer 20, the method 2700 may include a step of indicating to the authenticated user, via the display 104 or other control system components, which access drawer 20 contains the requested prescription 12, bag 14, prescription batch 11, or item, as depicted in block 2714. As noted above, this may be accomplished via the display 104, flashing lights, or any other indicating methods known in the art for providing instructions to a user.

Next, the method 2700 may include the steps of unlocking and/or unlatching the access drawer 20 with the requested prescription 12 deposited therein, as depicted in block 2716, and the user opening the access drawer 20, as depicted in block 2718. As noted above, unlatching and/or unlocking of the access drawers 20 and/or the access doors may be accomplished via the electronic drawer locks 94 described herein or other latches or electronic locks known in the art. The method 2700 may further include the steps of the user removing all of the contents from that storage container 22, as depicted in block 2720, the user closing the access drawer 20, as depicted in block 2722, and the control system 36 and/or the electronic drawer locks 94 automatically locking the access drawer 20 upon closure thereof, as depicted in block 2724. For example, there may be a sensor and/or mechanical trigger which automatically latches and/or electronically locks the access drawer 20 upon full closure of the access drawer 20.

The method 2700 may then include the steps of receiving and updating status information regarding that closed access drawer 20 in the memory storage device 100, as depicted in block 2726. Specifically, the control system 36 may receive signals from the drawer scanners 26 or sensors 30 of the access drawers 20 and/or transport system 24 indicating identification indicia 16 of the prescription batch 11 that was removed from the access drawer 20, indicating if the storage container 22 in the closed access drawer 20 is now empty or alternatively loaded with a new item and/or a returned prescription, indicating if the new item or returned prescription is too large or protruding above a top of the storage container 22, errors detected via the sensors 30 of the closed access drawer 20, etc. In some embodiments of the invention, the control system 36 may verify that the storage container 22 was returned to the closed access drawer 20, verify that the storage container 22 is empty if no return prescriptions were scanned, and/or verify that the storage container 22 is not empty if return prescriptions were scanned.

In some embodiments of the invention, the method 2700 may further include the steps of the control system 36 commanding the transport system 24 to travel to and deposit the storage container 22 from the closed access drawer 20 to an empty one of the compartments 40, as depicted in block 2728, for later retrieval. The dispensing and/or loading methods may then repeat any number of time for any number of prescription batches 11. Any of the access drawers 20 described herein may be configured to perform the storage and/or retrieval methods described herein without departing from the scope of the invention.

In some embodiments of the invention, either of the methods 2600,2700 described herein may further comprise a step of the transport system 24 and corresponding sensors 30 and/or transport scanner 28 performing a complete automated audit of the entire contents of the storage matrix 18. This audit may be performed, for example, after any access that involves opening the primary doors 44 of the outer housing 38 via the hinge mechanism 46 described above, or any other type of unlocking and opening that provides simultaneous access to multiple compartments 40 of the storage matrix 18 and/or access to the transport system 24. The control system 36 may be configured to, at regular or scheduled time intervals, place a map of items stored in the compartments 40 in an accessible location for use by technicians or pharmacy staff, particularly to assist users to items they are looking for if they need to open the primary doors 44. After the primary doors 44 are closed and secured after such manual access, the control system 36 may take physical inventory of all storage containers 22 and items in the compartments 40 and update records in the memory storage device 100 or associated databases accordingly, thus updating the map as well.

Furthermore, because a user may have reorganized the storage containers 22 while the primary doors 44 were opened, a verification process using a plurality of verification sensors may be utilized in some alternative embodiments of the invention. For example, five sets of emitter/collector sensor systems may be vertically positioned on each of the primary doors 44, one associated with each of five columns of slots in the storage matrix 18. This may allow the control system 36 to detect if any of the storage containers 22 have been moved into or out of the compartments 40 in a column of the storage matrix 18. Furthermore, this may allow the control system 36 to detect if any of the storage containers 22 are partially inserted into the compartments 40. These verification sensors may also be tripped by a user's hand or other object.

Upon closing the primary doors 44, the control system 36 may perform a minimal amount of cleanup functions, such as determining if any of the storage containers 22 are partially inserted into one of the compartments 40, and then the control system 36 may resume normal operations. Idle time may be used by the control system 36 to verify the occupants of compartments 40 in columns for which the emitter/collector sensors have shown activity. If the control system 36 determines that any of the storage containers 22 or an item is out of place, it may present the storage container 22 to the user via the transport system 24, such that the item can be removed and re-stored. If the control system 36 does not find an item that should be located in the prescription storage and retrieval system 10, it may keep looking for it using information from the verification sensors to priorities the search. The control system 36 may also provide an option to re-map the entire system if needed. If the missing item is still not found, an error notification may be provided to the user via the display 104 and/or the user interface 102.

In some embodiments of the invention, performance of the prescription storage and retrieval system 10 may be enhanced by optimizing storage locations for the storage containers 22. For example, the control system 36 may be configured to anticipate a need for item or prescription retrieval and command repositioning of an associated one of the storage containers 22 to a closer or more efficient location for speedy retrieval. This repositioning may occur at some point when the transport system 24 is not otherwise occupied with other tasks. Specifically, the control system 36 may be configured to allow an authorized user to position or reposition the storage containers 22 for efficient loading or retrieval based on various factors, such as time of day, tasks being undertaken, size of items being stored, patient load, and the like.

Additionally or alternatively, some technicians or authorized users may be provided access to manual storage and retrieval capabilities via the control system 36 and/or the display 104 or user interface 102. Specifically, the authorized user may command the trolley 86 to move to a particular compartment 40 of the user's choosing in the outer housing 38 or to a particular access drawer 20 or remote device to be removed from the prescription storage and retrieval system 10. This is in contrast to operating modes in which the control system 36 chooses where to send the storage containers 22 within the outer housing 38 based on readings from the sensors 30 and other factors described herein.

In some embodiments of the invention, either of the methods 2600,2700 described herein may also include a step of returning items to stock when they are not picked up by customers or other users in a timely manner. For example, one of the bulk storage areas described above may serve as a "return-to-stock" bin and may be secured with an electronic door lock, as described above. When the control system 36 determines that an item or prescription has not been picked up within a threshold amount of time, the control system 36 may command the transport system 24 to retrieve the item and dispense it into the return-to-stock bin. Access for a user to unlock and/or open the return-to-stock bin may be denied by the control system 36 while the transport system 24 is dispensing the relevant prescription batches 11 into the return-to-stock bin. When a prescription or stored item is dispensed into the return-to-stock bin, this may be communicated to the user via the display 104.

In some embodiments of the invention, if the return-to-stock bin is accessed by an authorized user, the control system 36 may interrupt the process of dispensing items into the return-to-stock bin while the user empties the return-to-stock bin. The control system 36 may then restart the process of dispensing items into the return-to-stock bin once the door locks thereof are again engaged. Sensors may also indicate to the control system 36 when the return-to-stock bin is full. This information may also be communicated to the display 104 or the user interface 102. The control system 36 may thus suspend any operations that add additional items to the return-to-stock bin until sensors indicate that the return-to-stock bin is no longer full. Finally, the control system 36 may provide a report showing items that have been transferred to the return-to-stock bin and items pending transfer once the return-to-stock bin has been emptied and the process restarted.

Either of the methods 2600,2700 described herein may also include a step of opening the storage matrix 18 to access the transport system 24 for service or repair. Specifically, this step may involve pivoting or rotating open the storage matrix 18 as a whole, or pivoting open a half or at least a portion of the outer housing 38 and compartments 40, such as opening of one of the primary doors 44. Then service personnel may access the transport system 24 behind the storage matrix 18 for maintenance, repairs, or updates thereto. The storage matrix 18 opening step may be controlled via the electronic door locks 32 and may require authentication via the control system 36. For example, service personnel may be given special cards and/or codes that they enter via the user interface 102 in order to verify to the control system 36 that they are authorized to access the transport system 24. Additionally or alternatively, access for opening the storage matrix 18 may be provided via a physical key inserted into the manual override lock 34, for use in cases of power failure or other failures in the control system 36, such as erroneous authentication failures. Such access may be recorded and stored via the lock memory device 35 described above.

Advantageously, the prescription storage and retrieval system 10 and methods described herein allow pharmacies to promptly serve patients arriving to pick up prescriptions, ensure that patients receive all their prescriptions, avoid dispensing the wrong prescription to a patient, ensure that a pharmacist has verified a prescription before it is given to the patient, prevent drug diversion, return to stock on a timely bases prescriptions that are not picked up, and utilize pharmacy working space efficiently.

Although the invention has been described with reference to the embodiments illustrated in the attached drawing figures, it is noted that equivalents may be employed and substitutions made herein without departing from the scope of the invention as recited herein. For example, in some embodiments of the invention, the items stored in the prescription storage and retrieval system 10 may be medical pathology specimen slides or other medical items requiring secure storage and retrieval. When stored in bulk, the medical pathology specimen slides may be part of a box or package of slides with a barcode on the box or package referencing a system that tracks the production, processing, analysis, utilization, and storage of the slides contained therein. Furthermore, the individual slides or sub-packages of slides within the box or package and other information related to the specific specimens may also be tracked via the prescription storage and retrieval system 10 described herein.

Having thus described one or more embodiments of the invention, what is claimed as new and desired to be protected by Letters Patent includes the following:

1. A storage and retrieval system, comprising:
   a storage matrix comprising:
   an outer housing having one or more access openings selectively accessible by a user, and a plurality of compartments located within the outer housing;
   a plurality of storage containers sized and configured to be removably received by one or more of the compartments or access openings;
   a transport system located within the outer housing, wherein the transport system is configured for detachably attaching to the storage containers and for selectively moving the storage containers to any of the compartments or access openings;
scanners configured for scanning identification indicia displayed on items placed in one of the storage containers;
a control system communicably coupled with the scanners and the transport system and configured for commanding the transport system to relocate any of the storage containers from one of the compartments or access openings to another of the compartments or access openings and for tracking locations or coordinates of the items based on the identification indicia on the items located in the storage containers, as scanned by the scanners and transmitted to the control system; and
one or more access drawers, each actuatable or extendable through one of the access openings, electronically lockable, and movable between an open position and a closed position, wherein the access drawers are configured to receive one of the storage containers therein, wherein the control system is further configured for commanding unlocking of one of the access drawers in which one of the storage containers is deposited;
wherein the scanners comprise one or more drawer scanners each associated with one of the access drawers in the storage matrix, wherein the drawer scanners automatically scan the identification indicia on the items in the storage containers within one of the access drawers as the one of the access drawers is being opened or closed; and
wherein each of the plurality of drawer scanners is facing upward, wherein at least one of the storage containers and the access drawers include bottom portions at least partially made of translucent material or bottom portions that have openings therethrough, such that the scanners scan the identification indicia through the bottom portions as the access drawers are being opened or closed.

2. The storage and retrieval system of claim 1, further comprising one or more electronic drawer locks, each associated with one of the access drawers, communicably coupled with the control system, and configured for preventing opening of an associated one of the access drawers in a locked configuration and allowing opening of the associated one of the access drawers in an unlocked configuration.

3. The storage and retrieval system of claim 1, wherein the control system comprises a processor, a memory storage device, a user interface, and at least one display, wherein the processor is configured for:
receiving authentication information from an administrator regarding what actions require authentication and what users have permission for those actions;
receiving identification information and a requested action from a user via the user interface,
commanding the display to indicate the user is not an authenticated user when the processor cannot match the identification information and the requested action with authentication information stored in the memory storage device, and
commanding at least one actuatable component of the storage and retrieval system communicably coupled to the control system, when the processor determines that the identification information and the requested action does match with the authentication information stored in the memory storage device or that the requested action does not require identification information, to at least one of:
retrieve a requested item,
unlock one of the access drawers that is empty or that contains the requested item, and
move one of the storage containers from one of the access drawers or one of the compartments to another one of the access drawers or another one of the storage compartments.

4. The storage and retrieval system of claim 1, further comprising a camera, wherein the camera is located within the outer housing, communicably coupled with the control system, and configured to record contents of one of the storage containers.

5. The storage and retrieval system of claim 1, further comprising a plurality of sensors each associated with one of the access drawers or the transport system and configured for detecting storage container content status information and sending the storage container content status to the control system.

6. The storage and retrieval system of claim 5, wherein detecting the storage container content status information comprises at least one of: detecting the presence of one of the storage containers therein, detecting whether the one of the storage containers is empty, and detecting if content in the one of the storage containers is protruding out of the storage container.

7. The storage and retrieval system of claim 1, wherein the transport system is located within the outer housing and behind the plurality of compartments, wherein at least a portion of the plurality of compartments and at least a portion of the outer housing of the storage matrix together form one or more primary doors that are pivotable in a direction away from the transport system, providing access to the transport system for servicing or updating.

8. The storage and retrieval system of claim 7, further comprising one or more electronic door locks each associated with one of the primary doors of the storage matrix, each communicably coupled with the control system and each configured for preventing opening of an associated one of the primary doors in a locked configuration and allowing opening of the associated one of the primary doors in an unlocked configuration.

9. A storage and retrieval system, comprising:
a storage matrix having a front side and an opposed back side, the storage matrix comprising:
an outer housing having one or more access openings each selectively accessible from the front side of the storage matrix by a user, and
a plurality of compartments in the outer housing;
a plurality of storage containers sized and configured to be removably received by one or more of the compartments and the access openings;
a transport system configured for detachably attaching to the storage containers and for selectively moving the storage containers to coordinates of any of the compartments or the access openings, wherein all of the compartments and the access openings are selectively accessible by the transport system from the back side of the storage matrix;
scanners configured for scanning identification indicia on items placed in one of the storage containers located at one of the access openings;

a control system communicably coupled with the scanners and the transport system and configured for:
receiving signals from one of the scanners, corresponding to identification indicia scanned by one of the scanners, indicating that a first item was loaded in a first one of the storage containers in one of the access openings,
commanding the transport system to relocate the first one of the storage containers to a selected one of the compartments in the storage matrix that is empty,
transmitting data that associates identification indicia for the first item and location information for the selected one of the compartments to a memory storage device accessible by the control system,
receiving a request from an authorized user to retrieve the first item,
commanding the transport system to retrieve the first one of the storage containers from the selected one of the compartments, and
commanding the transport system to move the first one of the storage containers to an empty one of the access openings and to deposit the first one of the storage containers into the empty one of the access openings for retrieval of the first item by the authorized user; and
one or more access drawers, each actuatable or extendable through one of the access openings, electronically lockable, and movable between an open position and a closed position, wherein the access drawers are configured to receive one of the storage containers therein, wherein the control system is further configured for commanding unlocking of a one of the access drawers in which the first one of the storage containers is deposited for loading or retrieval by the authorized user;
wherein the scanners comprise one or more drawer scanners each associated with one of the access drawers in the storage matrix, wherein each of the plurality of drawer scanners is facing upward, wherein the storage containers include bottom portions at least partially made of translucent material or bottom portions that have openings therethrough through which the scanners scan the identification indicia as the access drawers are being opened or closed.

10. The storage and retrieval system of claim 9, further comprising a plurality of sensors each associated with one of the access drawers and the transport system and configured for detecting storage container content status information, wherein detecting storage container content status information comprises at least one of: detecting the presence of one of the storage containers therein, detecting whether the one of the storage containers is empty, and detecting if content in the one of the storage containers is protruding out of the storage container.

11. The storage and retrieval system of claim 9, wherein the control system comprises a processor, a memory storage device, a user interface, and at least one display, wherein the processor is configured for:
receiving authentication information from an administrator regarding what actions require authentication and what users have permission for those actions;
receiving identification information and a requested action from a user via the user interface,
commanding the display to indicate the user is not an authenticated user when the processor cannot match the identification information and the requested action with authentication information stored in the memory storage device, and
commanding at least one actuatable component of the storage and retrieval system communicably coupled to the control system, when the processor determines that the identification information and the requested action does match with the authentication information stored in the memory storage device or that the requested action does not require identification information, to at least one of:
retrieve a requested item,
unlock one of the access drawers that is empty or that contains the requested item,
move one of the storage containers from one of the access drawers or one of the compartments to another one of the access drawers or another one of the storage compartments, and
update the memory storage device indicating a location within the storage matrix where the one of the storage containers was moved.

12. The storage and retrieval system of claim 9, further comprising one or more electronic door locks each associated with one of the primary doors of the storage matrix, each communicably coupled with the control system and each configured for preventing opening of an associated one of the primary doors in a locked configuration and allowing opening of the associated one of the primary doors in an unlocked configuration.

13. The storage and retrieval system of claim 9, further comprising a camera, wherein the camera is located within the outer housing, communicably coupled with the control system, and configured to record contents of one of the storage containers.

14. A storage and retrieval system, comprising:
a first storage matrix comprising:
an outer housing having one or more access openings formed therethrough, and
a plurality of compartments located in the outer housing arranged in a plurality of rows and columns, wherein at least a portion of the plurality of compartments and at least a portion of the outer housing of the storage matrix together form one or more primary doors that are selectively openable;
one or more access drawers, each electronically lockable, each actuatable or extendable through one of the access openings, and each movable between an open position and a closed position;
a plurality of storage containers each sized and configured to be removably received within one or more of the compartments and the access openings of the storage matrix, wherein the access drawers are configured to receive one of the storage containers;
a first transport system configured for detachably attaching to one or more of the storage containers and for selectively moving the storage containers to coordinates of any of the compartments or access drawers, wherein the first transport system is located within the outer housing and behind the plurality of compartments, wherein at least a portion of the plurality of compartments and at least a portion of the outer housing of the storage matrix are together pivotable in a direction away from the first transport system, providing access to the first transport system for servicing or updating;
one or more drawer scanners each associated with one of the access drawers in the storage matrix, each of the drawer scanners being configured for scanning identification indicia on items placed in one of the storage containers located within one of the access drawers;
a plurality of sensors each associated with one of the access drawers and first transport system and configured for detecting storage container content status information, wherein detecting storage container content status information comprises at least one of: detecting the presence of one of the storage containers therein, detecting whether the one of the storage containers is empty, and detecting if content in the one of the storage containers is protruding out of the storage container;
a camera located within the outer housing and configured to record content of the storage container; and
a control system communicably coupled with the drawer scanners, the sensors, the camera, and the first transport system and configured for:
commanding unlocking of one of the access drawers;
receiving signals from one of the drawer scanners, corresponding to identification indicia scanned by one of the drawer scanners, indicating that a first item was loaded in a first one of the storage containers in one of the access drawers,
commanding the first transport system to relocate the first one of the storage containers to a selected one of the compartments in the storage matrix that is empty,
storing data that associates identification indicia for the first item and location information for the selected one of the compartments into a memory storage device accessible by the control system,
receiving a request from an authorized user to retrieve the first item,
commanding the first transport system to retrieve the first one of the storage containers from the selected one of the compartments,
commanding the first transport system to move the first transport system to an empty one of the access drawers,
commanding the first transport system to deposit the first one of the storage containers into the empty one of the access drawers, and
commanding unlocking of the access drawer in which the first one of the storage containers is deposited,
a second storage matrix,
wherein the outer housing of the first transport system has at least one transfer opening which, when coupled with the second storage matrix, provides access to transfer storage containers between the first storage matrix and the second storage matrix.

15. The storage and retrieval system of claim 14, wherein detecting storage container content status information comprises at least one of: detecting the presence of one of the storage containers therein, detecting whether the one of the storage containers is empty, and detecting if content in the one of the storage containers is protruding out of the storage container.

16. The storage and retrieval system of claim 14, wherein the control system comprises a processor, a memory storage device, a user interface, and at least one display, wherein the processor is configured for:
receiving authentication information from an administrator regarding what actions require authentication and what users have permission for those actions;
receiving identification information and a requested action from a user via the user interface,
commanding the display to indicate the user is not an authenticated user when the processor cannot match the identification information and the requested action with authentication information stored in the memory storage device, and
commanding at least one actuatable component of the storage and retrieval system communicably coupled to the control system, when the processor determines that the identification information and the requested action does match with the authentication information stored in the memory storage device or that the requested action does not require identification information, to at least one of:
retrieve a requested item, and
unlock one of the access drawers that is empty or that contains the requested item,
move one of the storage containers from one of the access drawers or one of the compartments to another one of the access drawers or another one of the storage compartments,
update the memory storage device indicating a location within the storage matrix where the one of the storage containers was moved, and
unlock one or more of the primary doors.

17. A storage and retrieval system, comprising:
a first storage matrix comprising:
an outer housing having one or more access openings formed therethrough, and
a plurality of compartments located in the outer housing arranged in a plurality of rows and columns, wherein at least a portion of the plurality of compartments and at least a portion of the outer housing of the storage matrix together form one or more primary doors that are selectively openable;
one or more access drawers, each electronically lockable, each actuatable or extendable through one of the access openings, and each movable between an open position and a closed position;
a plurality of storage containers each sized and configured to be removably received within one or more of the compartments and the access openings of the storage matrix, wherein the access drawers are configured to receive one of the storage containers;
a first transport system configured for detachably attaching to one or more of the storage containers and for selectively moving the storage containers to coordinates of any of the compartments or access drawers, wherein the first transport system is located within the outer housing and behind the plurality of compartments, wherein at least a portion of the plurality of compartments and at least a portion of the outer housing of the storage matrix are together pivotable in a direction away from the first transport system, providing access to the first transport system for servicing or updating;
one or more drawer scanners each associated with one of the access drawers in the storage matrix, each of the drawer scanners being configured for scanning identification indicia on items placed in one of the storage containers located within one of the access drawers;
a plurality of sensors each associated with one of the access drawers and first transport system and configured for detecting storage container content status information, wherein detecting storage container content status information comprises at least one of: detecting the presence of one of the storage containers therein, detecting whether the one of the storage containers is empty, and detecting if content in the one of the storage containers is protruding out of the storage container;
a camera located within the outer housing and configured to record content of the storage container;
a control system communicably coupled with the drawer scanners, the sensors, the camera, and the first transport system and configured for:
commanding unlocking of one of the access drawers;
receiving signals from one of the drawer scanners, corresponding to identification indicia scanned by one of the drawer scanners, indicating that a first item was loaded in a first one of the storage containers in one of the access drawers,
commanding the first transport system to relocate the first one of the storage containers to a selected one of the compartments in the storage matrix that is empty,
storing data that associates identification indicia for the first item and location information for the selected one of the compartments into a memory storage device accessible by the control system,
receiving a request from an authorized user to retrieve the first item,
commanding the first transport system to retrieve the first one of the storage containers from the selected one of the compartments,
commanding the first transport system to move the first transport system to an empty one of the access drawers,
commanding the first transport system to deposit the first one of the storage containers into the empty one of the access drawers,
commanding unlocking of the access drawer in which the first one of the storage containers is deposited; and
an insert installed in at least one of the storage containers and configured to hold one or more items securely in a desired orientation for scanning by the drawer scanners.

18. A storage and retrieval system, comprising:
a first storage matrix comprising:
an outer housing having one or more access openings formed therethrough, and
a plurality of compartments located in the outer housing arranged in a plurality of rows and columns, wherein at least a portion of the plurality of compartments and at least a portion of the outer housing of the storage matrix together form one or more primary doors that are selectively openable;
one or more access drawers, each electronically lockable, each actuatable or extendable through one of the access openings, and each movable between an open position and a closed position;
a plurality of storage containers each sized and configured to be removably received within one or more of the compartments and the access openings of the storage matrix, wherein the access drawers are configured to receive one of the storage containers;
a first transport system configured for detachably attaching to one or more of the storage containers and for selectively moving the storage containers to coordinates of any of the compartments or access drawers, wherein the first transport system is located within the outer housing and behind the plurality of compartments, wherein at least a portion of the plurality of compartments and at least a portion of the outer housing of the storage matrix are together pivotable in a direction away from the first transport system, providing access to the first transport system for servicing or updating;
one or more drawer scanners each associated with one of the access drawers in the storage matrix, each of the drawer scanners being configured for scanning identification indicia on items placed in one of the storage containers located within one of the access drawers;
a plurality of sensors each associated with one of the access drawers and first transport system and configured for detecting storage container content status information, wherein detecting storage container content status information comprises at least one of: detecting the presence of one of the storage containers therein, detecting whether the one of the storage containers is empty, and detecting if content in the one of the storage containers is protruding out of the storage container;
a camera located within the outer housing and configured to record content of the storage container; and
a control system communicably coupled with the drawer scanners, the sensors, the camera, and the first transport system and configured for:
commanding unlocking of one of the access drawers;
receiving signals from one of the drawer scanners, corresponding to identification indicia scanned by one of the drawer scanners, indicating that a first item was loaded in a first one of the storage containers in one of the access drawers,
commanding the first transport system to relocate the first one of the storage containers to a selected one of the compartments in the storage matrix that is empty,
storing data that associates identification indicia for the first item and location information for the selected one of the compartments into a memory storage device accessible by the control system,
receiving a request from an authorized user to retrieve the first item,
commanding the first transport system to retrieve the first one of the storage containers from the selected one of the compartments,
commanding the first transport system to move the first transport system to an empty one of the access drawers,
commanding the first transport system to deposit the first one of the storage containers into the empty one of the access drawers,
commanding unlocking of the access drawer in which the first one of the storage containers is deposited;
the transport system further comprising a trolley actuatable for retrieving and relocating the storage compartments within the storage matrix and at least one laser mapping sensor on the trolley, configured for properly aligning the trolley with the compartments or the access drawers.

* * * * *